(12) United States Patent
Dore et al.

(10) Patent No.: US 8,597,884 B2
(45) Date of Patent: Dec. 3, 2013

(54) PROCESS CONTROLS FOR MOLECULAR ASSAY

(75) Inventors: Benoit Dore, Quebec (CA); Christian Menard, Quebec (CA); Tobin Hellyer, Sparks, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/417,025

(22) Filed: Mar. 9, 2012

(65) Prior Publication Data

US 2012/0282605 A1 Nov. 8, 2012

Related U.S. Application Data

(60) Provisional application No. 61/450,955, filed on Mar. 9, 2011.

(51) Int. Cl.
| | |
|---|---|
| *C12Q 1/68* | (2006.01) |
| *C12Q 1/00* | (2006.01) |
| *C12Q 1/70* | (2006.01) |
| *C12Q 1/34* | (2006.01) |
| *C12Q 1/37* | (2006.01) |
| *G01N 33/53* | (2006.01) |
| *C12N 9/36* | (2006.01) |
| *C12N 9/54* | (2006.01) |
| *C12N 1/20* | (2006.01) |
| *C12M 1/34* | (2006.01) |

(52) U.S. Cl.
USPC ........ 435/6.1; 435/4; 435/5; 435/7.2; 435/18; 435/23; 435/206; 435/221; 435/252.31; 435/287.2

(58) Field of Classification Search
USPC ............... 435/4, 5, 6.1, 7.2, 18, 23, 206, 221, 435/252.31, 287.2
See application file for complete search history.

(56) References Cited

U.S. PATENT DOCUMENTS

| | | |
|---|---|---|
| 7,282,350 B2 | 10/2007 | Rao et al. |
| 8,021,848 B2 | 9/2011 | Straus |
| 2006/0166233 A1 | 7/2006 | Wu et al. |
| 2007/0015139 A1 * | 1/2007 | Gayral et al. ............. 435/5 |
| 2009/0131650 A1 | 5/2009 | Brahmasandra et al. |
| 2011/0275090 A1 | 11/2011 | Hilligoss et al. |

FOREIGN PATENT DOCUMENTS

| | | | |
|---|---|---|---|
| WO | WO 99/06594 | * | 2/1999 |
| WO | WO 2008/134464 | * | 11/2008 |

OTHER PUBLICATIONS

Niwa et al, Lytic enzyme, labiase for a broad range of Gram-positive bacteria and its application to analyze functional DNA/RNA, 2005, Journal of Microbiological Methods, 61, 251-260.*
Vuolanto et al, Phytase production by high cell density culture of recombinant *Bacillus subtilis*, 2001, Biotechnology Letters 23: 761-766.*
Bricker et al, Evaluation of the *Brucella abortus* species-specific polymerase chain reaction assay, an improved version of the *Brucella* AMOS polymerase chain reaction assay for cattle, 2003, J Vet Diagn Invest 15:374-378.*
James et al, Construction of genetically engineered *Streptococcus gordonii* strains to provide control in QPCR assays for assessing microbiological quality of recreational water, 2008, Journal of Applied Microbiology, 105, 2213-2222.*
Long et al, Development of a quantitative polymerase chain reaction method using a live bacterium as internal control for the detection of *Listeria monocytogenes*, 2008, Diagnostic Microbiology and Infectious Disease 62, 374-381.*
International Search Report and Written Opinion dated May 25, 2012 for Application No. PCT/US2012/028603, filed Mar. 9, 2012.

* cited by examiner

*Primary Examiner* — Narayan Bhat
(74) *Attorney, Agent, or Firm* — Knobbe Martens Olson & Bear, LLP

(57) ABSTRACT

A full process control for use with a molecular assay and a method of determine the efficacy of the molecular assay. A full process control can include a fixed cell, and specifically can include a fixed vegetative cell. A method of determining the efficacy of a molecular assay can include providing an internal control, mixing the internal control with a sample, lysing the internal control and the sample, and detecting the lysis product. The full process control and/or the internal control can be *Bacillus subtilis* cells.

16 Claims, 14 Drawing Sheets

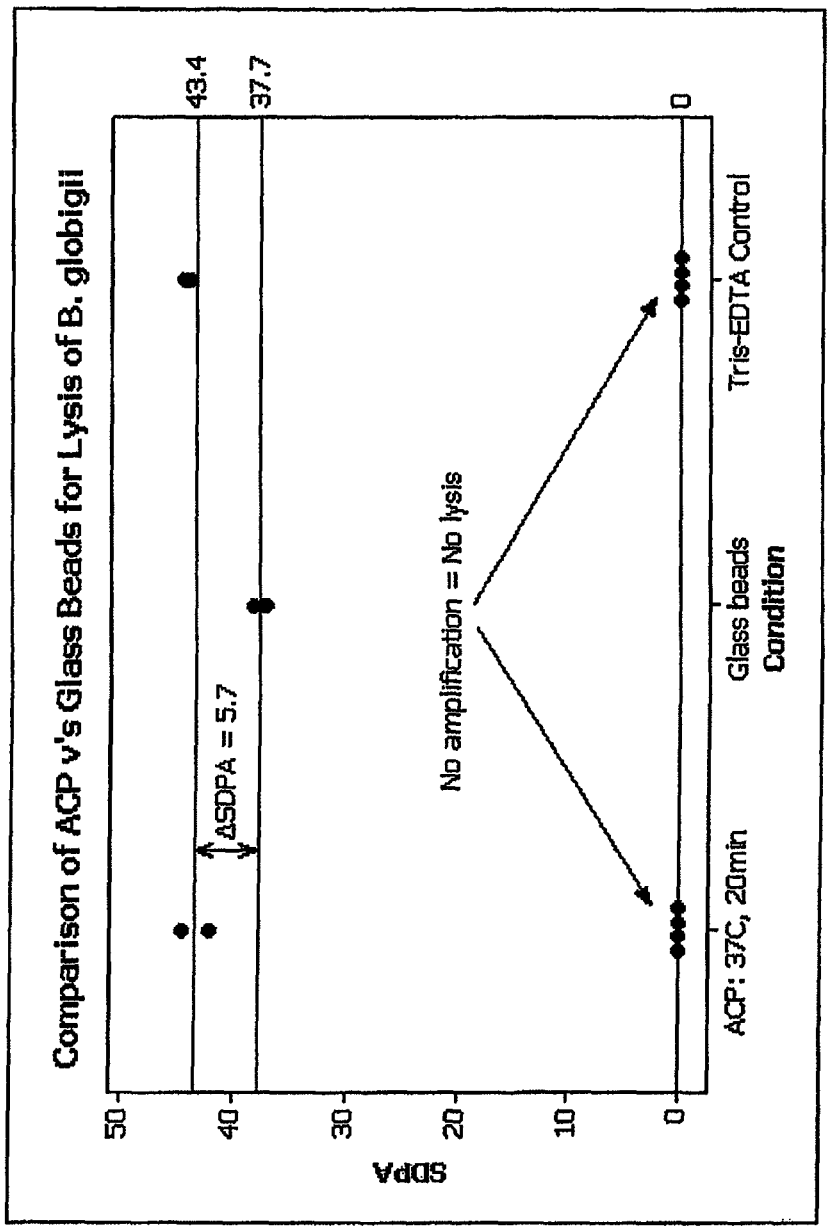
Figure 3. Comparison of ACP and Glass Beads for Lysis of *B. globigii*

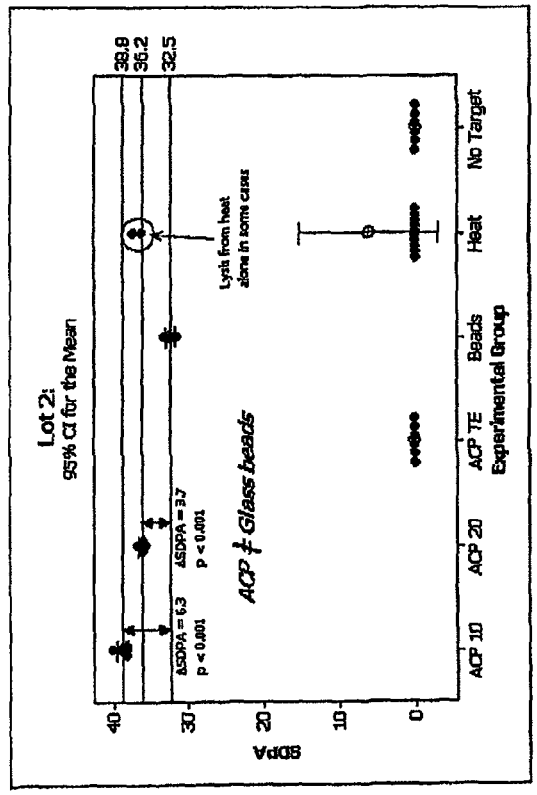
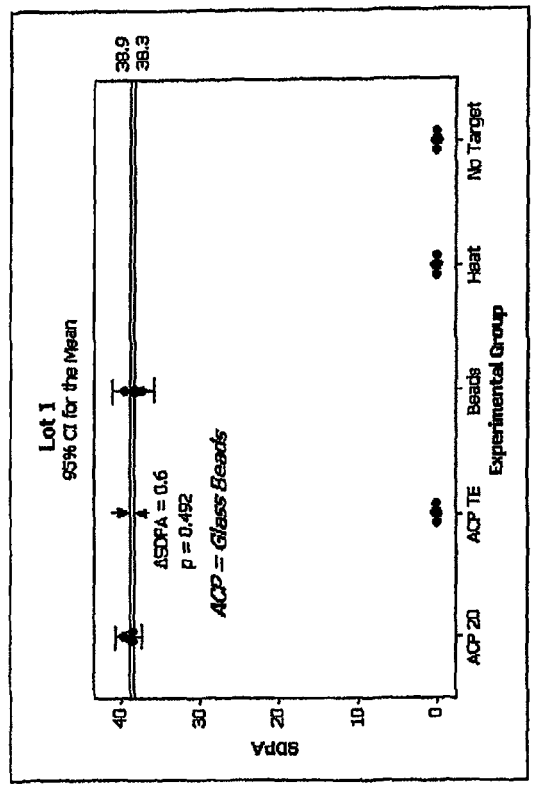
Figure 4. Comparison of ACP-dependent lysis between lots of *B. subtilis* spores

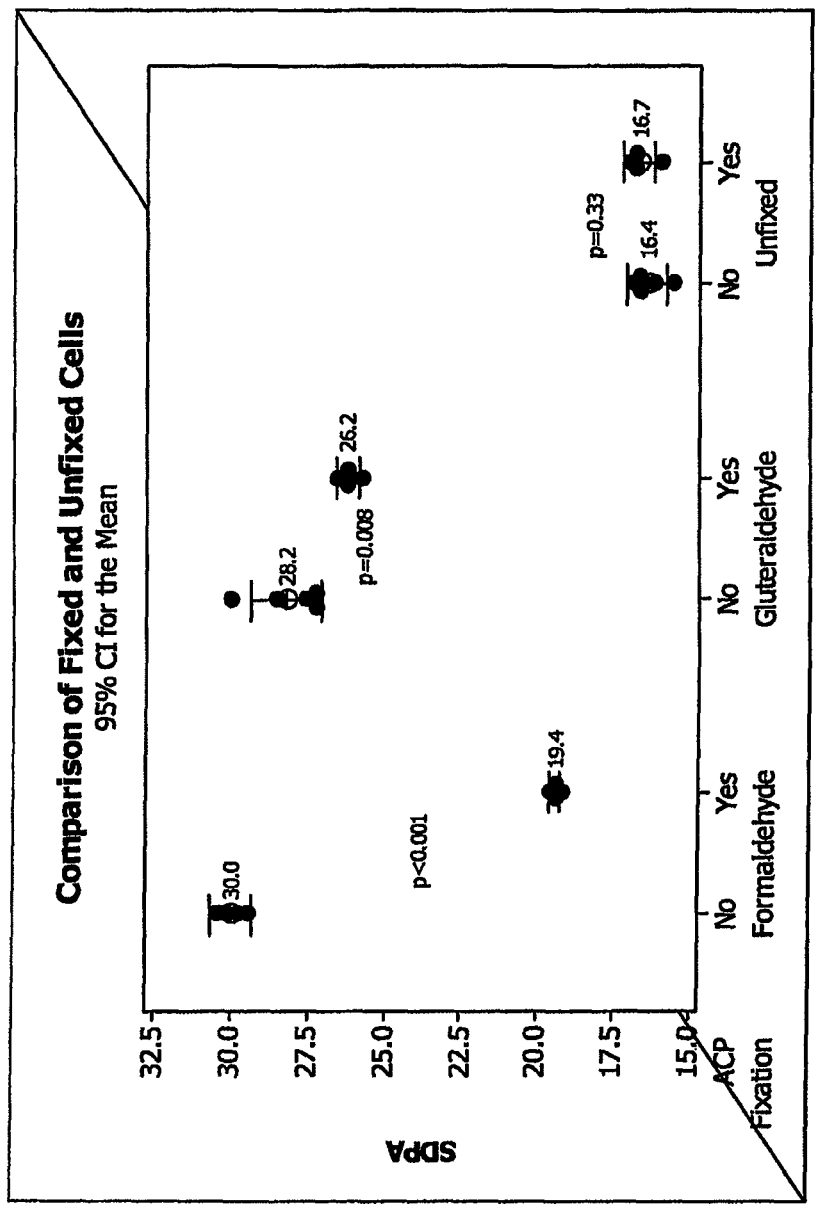
Figure 5. Comparison of fixed and unfixed cells of B. subtilis

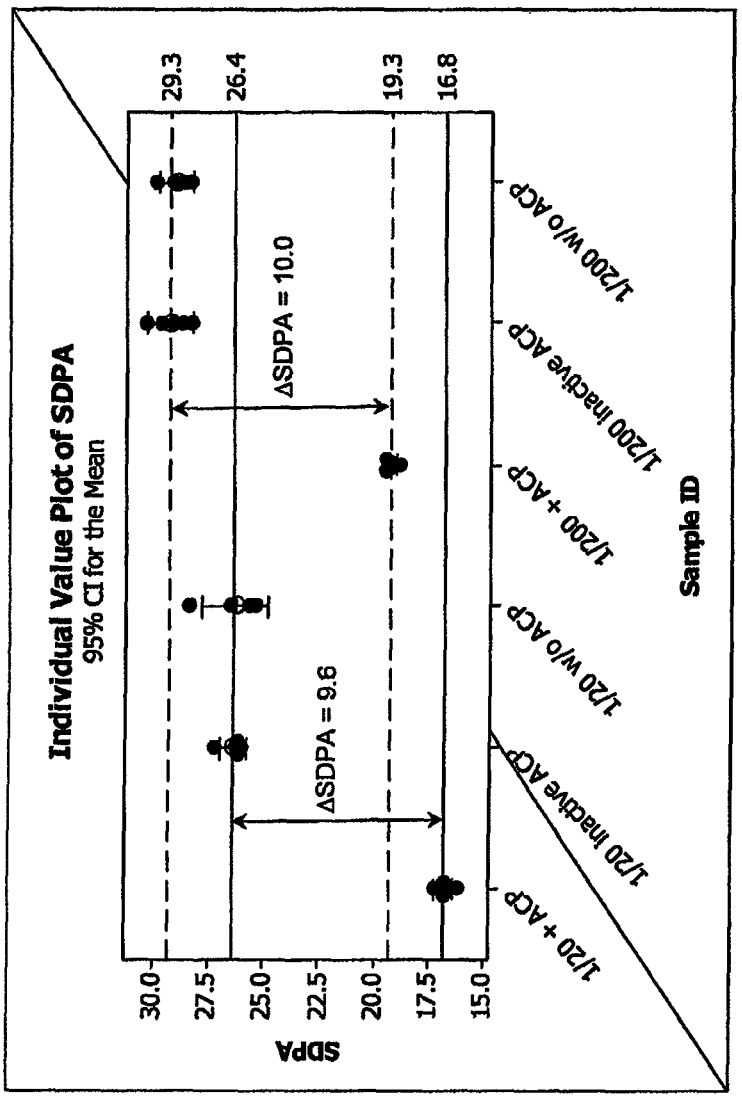
Figure 6. Susceptibility of formalin-fixed cells to ACP

PROCESS CONTROLS FOR MOLECULAR ASSAY

CROSS-REFERENCE TO RELATED APPLICATIONS

This application claims priority to U.S. Provisional Patent Application No. 61/450,955, entitled "PROCESS CONTROLS FOR MOLECULAR ASSAY," filed Mar. 9, 2011, the entire content of which is hereby incorporated by reference.

BACKGROUND

1. Field of the Invention

The specification relates to the field of controls for molecular assays.

2. Description of the Related Art

The accuracy and reliability of assay procedures are typically monitored through the use of controls. These controls include external controls and internal controls, either of which may be used to monitor all or part of the pre-analytical and analytical process.

External controls are performed by parallel analysis of separate samples containing the control substance alongside the test samples. In contrast, an internal control is performed through analysis of both the sample and the control substance in the same vessel and is typically spiked into the test sample prior to or during the testing process. Partial process controls are used to verify the results of specific steps of an assay (e.g., nucleic acid extraction or amplification and detection). In contrast, full process controls are used to verify the results of all steps of the assay (e.g., organism lysis, nucleic acid extraction, amplification and detection).

Each type of control presents advantages and disadvantages. Thus, while a full process control enables utilization of a single control to verify successful completion of each step of the assay, design of a full process control is more demanding than design of a partial process control. Internal full process controls that are introduced into the test sample prior to analysis have been successfully developed for use with molecular assays that rely on mechanical shearing from glass beads to lyse cells. However, for some applications it is not feasible or desirable to employ mechanical lysis and chemical or enzymatic processes must be employed. For example, for the purposes of process automation it may not be practicable to employ a means of mechanical shearing to induce lysis and alternative means must be sought to release cellular components of interest, e.g., nucleic acids, proteins, and the like. Accordingly, many molecular testing systems employ alternative, less generic means of cell lysis other than mechanical shearing. Process controls that are designed for use in the context of mechanical lysis are therefore not necessarily appropriate for control of processes involving alternative, more specific means of cell disruption such as those using chemical or enzymatic treatments that target specific components of the cell wall, membrane or capsule.

One alternate lysing technique relies on the use of the enzyme achromopeptidase ("ACP"). In such a procedure, ACP is used as a component in a solution that lyses cells, and in some cases digests the clinical matrix to facilitate the removal of inhibitors to downstream process steps, including for example, nucleic acid extraction, amplification, and detection. There is a need for internal full process controls for use in connection with processes involving chemical lysing agents, such as ACP.

BRIEF DESCRIPTION OF THE DRAWINGS

FIG. 3 displays test results from ACP treatment of *Bacillus globigii* spores.

FIG. 4 displays test results from ACP treatment of *Bacillus subtilis* spores.

FIG. 5 displays test results from ACP treatment of vegetative cells of *B. subtilis* (fixed or unfixed).

FIG. 6 displays test results of ACP treatment of fixed vegetative cells of *B. subtilis*.

SUMMARY

Figure 1:
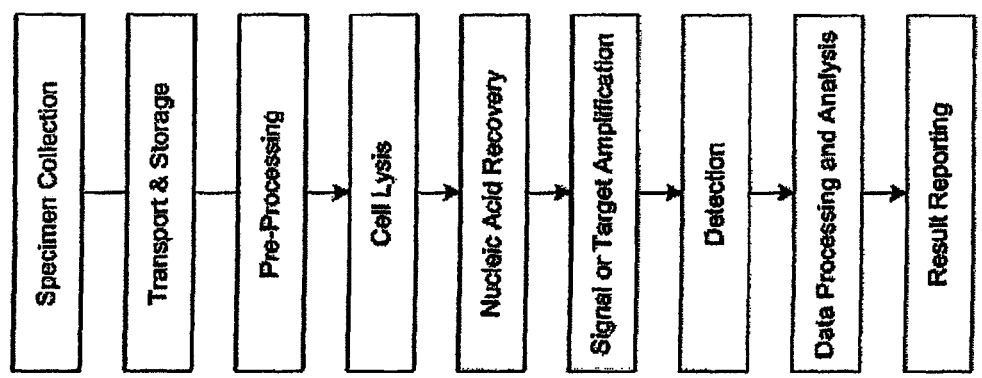
FIG. 1 depicts typical process steps involved in a nucleic acid amplification test ("NAAT")

Some embodiments disclosed herein relate generally to method of determining the efficacy of enzymatic cell lysis and to full process controls for molecular assays, and methods of making full process controls for molecular assays.

Some embodiments relate to a method of determining the efficacy of enzymatic cell lysis. The method can include, for example, providing an internal control that can, for example, include a plurality of bacterial cells that have been fixed with a fixing compound, mixing the internal control with a sample, lysing the internal control and the sample with a lysing agent, and detecting a lysis product.

In some aspects of the method, the fixed bacterial cells can be *Bacillus* cells. For example, in some embodiments, the fixed bacterial cells can be *Bacillus subtilis* cells that were contacted with a fixing compound during vegetative growth, i.e., fixed, vegetative *B. subtilis* cells.

In some aspects the bacteria can be recombinant cells that can, for example, include an internal control DNA sequence.

In some aspects, the control nucleic acid sequence can include a heterologous sequence, a *B. subtilis* sequence, or a sequence that is integrated into the host chromosome. In some embodiments, the control nucleic acid sequence can be present on a plasmid, bacteriophage, or the like.

In some aspects of the method, the fixed bacterial cells have been fixed by contacting the cells with a fixing agent, e.g., formalin/formaldehyde, glutaraldehyde, paraformaldehyde, or the like. For example, in some embodiments, the fixed bacterial cells are *Bacillus subtilis* that have been formalin fixed.

In some aspects of the method, the bacterial cells can be washed, e.g., either before or after they have been contacted with the fixing agent. For example, in some embodiments, the internal control comprises fixed, vegetative *Bacillus subtilis* cells that have been washed. In some aspects of the method, the detecting step can include performing an amplification reaction and detecting an amplicon.

In some aspects of the method, the lysing step comprises contacting the sample with a lysing agent. In some aspects, the lysing agent can be a lysing enzyme or a combination of lysing enzymes, e.g., achromopeptidase, lysozyme, lysotraphin, zymolase, cellulase, mutanolysin, glycanase, proteinase K, pronase, or any combination thereof. In some aspects of the method, the lysing agent can be an ionic detergent such as sodium or lithium dodecyl sulphate, a non-ionic detergent such as Triton X100 or Tween-20, a chaotrope such as guanidinium hydrochloride, ethanol or urea or a reducing agent such as β-mercaptoethanol, dithiothreitol (DTT) or tris (carboxyethyl)phosphine (TCEP). In some embodiments, the lytic agent may be a combination of lysing enzymes, detergents, chaotropes and/or reducing agents.

Some embodiments relate to methods of determining the efficacy of enzymatic cell lysis. The method can include providing an internal control that can include, for example, a plurality of fixed cells, mixing the internal control with a sample, lysing the internal control and the sample with an enzyme such as, for example, achromopeptidase, and detecting a lysis product.

In some aspects of the method, the fixed cells can include fixed *Bacillus subtilis* cells which can be, for example, vegetative cells. These vegetative cells can include, for example, recombinant cells that can, for example, include an internal control nucleic acid sequence. In some embodiments, the internal control nucleic acid is a heterologous nucleic acid. The internal nucleic acid sequence can, for example, be integrated into the host chromosome, and in some aspects, stably integrated into the host chromosome. In some embodiments, the internal control nucleic acid is present as an extra-chromosomal nucleic acid, e.g., on a plasmid, bacteriophage chromosome, or the like. In some aspects of the method, the fixed *Bacillus subtilis* cells are formalin fixed.

In some aspects of the method, preparing the internal control includes washing the *Bacillus subtilis* cells, which can include, for example, fixed or unfixed *Bacillus subtilis* cells.

Some embodiments relate to a method of monitoring the isolation, amplification, and detection of nucleic acids from a sample. In some embodiments, the method can include, providing an internal control that can include a plurality of bacterial cells that have been fixed with a fixing compound and which bacterial cells can include a control nucleic acid sequence, mixing the internal control with the sample to create a mixture, isolating nucleic acids from the mixture, amplifying the isolated nucleic acids to generate an amplicon, and detecting the amplicon.

In some aspects of the method of monitoring the isolation, amplification, and detection of nucleic acids from a sample, the bacterial cells are vegetative *Bacillus subtilis* cells. In some aspects of the method of monitoring the isolation, amplification, and detection of nucleic acids from a sample, the fixing compound can be selected from the group including formaldehyde, paraformaldehyde, glutaraldehyde, and any combination thereof. In some aspects of the method of monitoring the isolation, amplification, and detection of nucleic acids from a sample, the fixed bacterial cells can include recombinant cells.

In some aspects of the method of monitoring the isolation, amplification, and detection of nucleic acids from a sample, the plurality of fixed cells are washed prior to mixing the internal control with the sample and/or the plurality of fixed cells have been washed prior to being fixed.

In some aspects of the method of monitoring the isolation, amplification, and detection of nucleic acids from a sample, the internal control is dried and/or the internal control is lyophilized.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

DETAILED DESCRIPTION

The following description and examples illustrate preferred embodiments of the present invention in detail. Those of skill in the art will recognize that there are numerous variations and modifications of this invention that are encompassed by its scope. Accordingly, the description of a preferred embodiment should not be deemed to limit the scope of the present invention. In this description, reference is made to the drawings wherein like parts are designated with like numerals throughout.

The embodiments disclosed herein are based, in part, upon the discovery of a specimen process control that is useful to monitor various aspects of processing in connection with molecular assays, such as nucleic acid testing assays. As discussed herein, it was discovered that fixed cells can be advantageously used to monitor processing of samples involving the use of enzymatic or chemical agents to lyse cells. Accordingly, some embodiments disclosed herein relate to methods of preparing controls, i.e., a specimen processing control ("SPC"), for use in connection with a molecular assay and methods of using these controls, i.e., SPC, in connection with a molecular assay, as well as methods of making an SPC. In some embodiments, a control, i.e., SPC, for use in connection with a molecular assay is prepared by selecting cells that are susceptible to lysis under desired conditions. In some embodiments, these cells may be fixed bacterial cells, such as vegetative *Bacillus* cells. In some embodiments, the controls, i.e., SPC, can be used for verifying the results of all steps of a molecular assay. In other embodiments, controls, i.e., SPC, can be used for verifying the results of select steps of a molecular assay. However, a person skilled in the art will appreciate that the methods of control, i.e., SPC, and control preparation, i.e., SPC preparation, disclosed herein can be applied to any type of molecular assay, including hybridization assays, PCR or other amplification assays, direct sequencing, and other molecular diagnostic assays.

Analysis of biological samples often includes determining whether one or more polynucleotides or nucleic acids (e.g., a DNA, RNA, mRNA, or rRNA) are present in the sample. Such a determination can be made through a variety of analyses. One embodiment of an analysis for determining the presence of one or more polynucleotides is a nucleic acid amplification test ("NAAT"). Steps of some embodiments of a NAAT test are depicted in FIG. 1. These steps include collecting a specimen for analysis, transport and storage of the specimen, pre-processing of the specimen, lysis of cells or viruses within the specimen, nucleic acid recovery from the lysed cells or viruses, signal or target amplification, detection of the amplified signal or target, data processing and analysis, and result reporting.

Figure 2A:
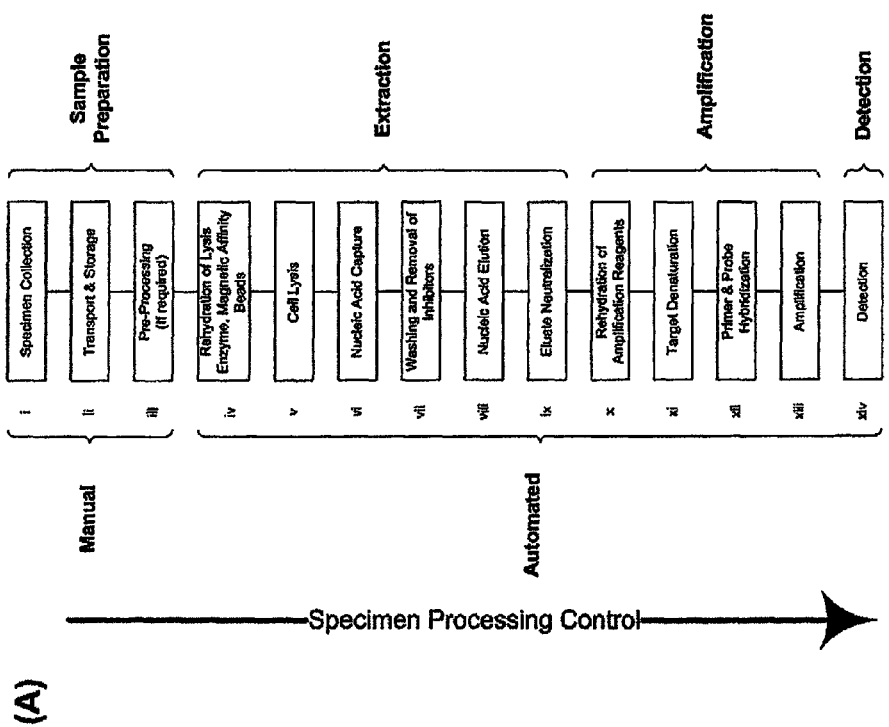
FIG. 2a depicts an embodiment of a method of use of a control in connection with a molecular assay. In the method of this figure, the SPC can be contained within the specimen transport device and can be used to monitor the efficacy of steps ii-xiv, including specimen transport and storage, cell lysis, nucleic acid recovery, amplification and detection.
Figure 2B:
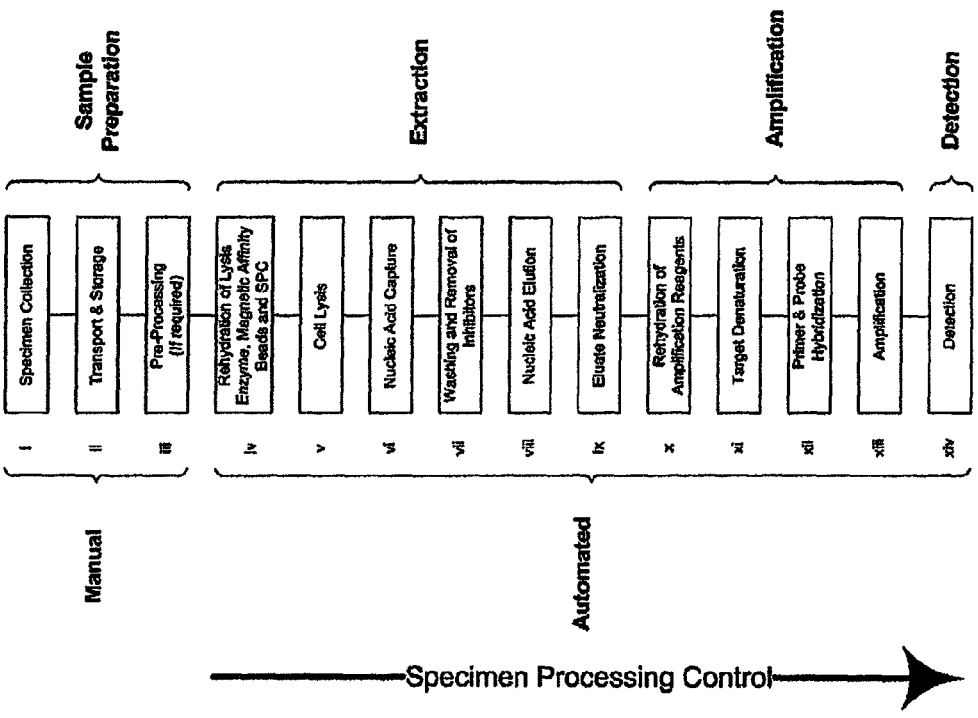
FIG. 2b depicts an embodiment of a method of use of a control in connection with a molecular assay. In the method of this figure, SPC can be dried with the extraction reagents, which can be, for example, magnetic affinity beads and lysis enzyme, and can be rehydrated with the sample to enable monitoring of the efficacy of steps iv-xiv, including, cell lysis, nucleic acid recovery, amplification and detection.
Figure 2C:
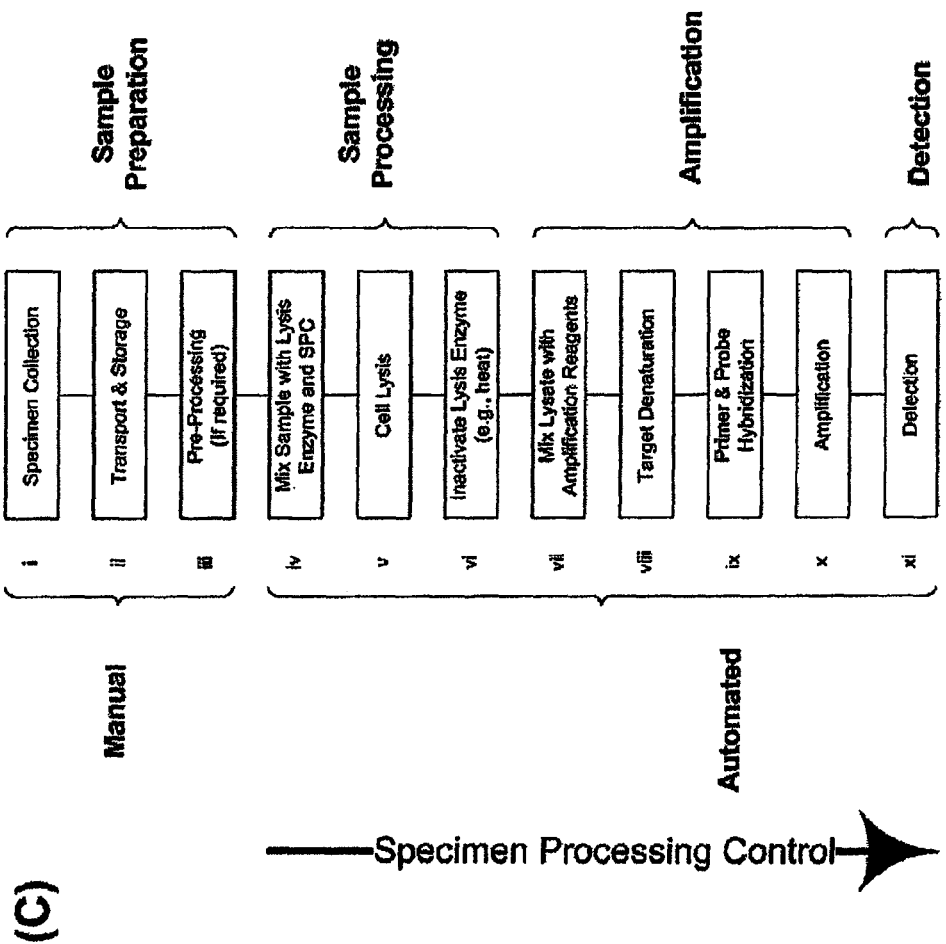
FIG. 2c depicts an embodiment of a method of use of a control in connection with a molecular assay. In the method of this figure, SPC can be dried with the lysis enzyme and can be rehydrated with the sample to enable monitoring of the efficacy of steps iv-xi including cell lysis, nucleic amplification and detection.

FIGS. 2a through 2c depict several embodiments of methods using a control, i.e., SPC, in connection with various steps within an exemplary molecular assay.

FIGS. 2a and 2b depict embodiments of use of a control, e.g., SPC, in connection with a molecular assay. More specifically, FIGS. 2a and 2b depict embodiments of use of a molecular assay control, i.e., SPC, in connection with an assay performed on the BD MAX™ assay system (Becton Dickinson, Franklin Lakes, N.J.), an automated testing platform for molecular diagnostics, including multiplex PCR. Steps of this assay are divided into manually performed steps and automated steps. These steps are further categorized as relating to sample preparation, extraction, amplification, and detection. In some embodiments, sample preparation steps are manually performed and the extraction, amplification, and detection steps are automatically performed. A person skilled in the art will recognize that the steps of a molecular assay can vary, and that the division of steps of a molecular assay can likewise vary.

Some embodiments of sample preparation steps, as depicted in FIGS. 2a and 2b, comprise specimen collection, specimen transport and storage, and pre-processing of the specimen. In some embodiments of sample preparation steps, pre-processing of the specimen may be performed, while other embodiments of sample preparation steps exclude pre-processing of the specimen. The skilled artisan will appreciate that in some embodiments, the pre-processing can be automated or manually performed.

Extraction steps of some embodiments of molecular assays, as depicted in 2a, can comprise rehydration of a lysis enzyme and/or chemical agent(s) and magnetic affinity beads, cell lysis, nucleic acid capture, washing and removal of inhibitors, nucleic acid elution, and eluate neutralization. Extraction steps of some embodiments of a molecular assay, as depicted in FIG. 2b, can comprise rehydration of lysis enzyme and/or chemical agent(s), magnetic affinity beads, and a control, e.g., SPC, cell lysis, nucleic acid capture, washing and removal of inhibitors, nucleic acid elution, and eluate neutralization.

Amplification steps of specific embodiments of a molecular assay, as depicted in FIGS. 2a and 2b, can comprise rehydration of amplification reagents, target denaturation, primer and probe hybridization, and amplification. Finally, detection steps of specific embodiments of a molecular assay, as depicted in FIGS. 2a and 2b can comprise, for example, homogeneous real-time fluorescent detection. Although FIG. 2 depicts a nucleic acid amplification reaction, the skilled artisan will readily appreciate that the specimen process controls disclosed herein can be used in connection with other molecular assays, such as nucleic acid testing, that do not necessarily involve an amplification step, e.g., in hybridization assays, or the like. The skilled artisan will also appreciate that the specimen process controls disclosed herein can be advantageously used with various types of nucleic acid amplification assays, including, for example, polymerase chain reaction (PCR), strand displacement amplification (including thermophilic SDA), ligase Chain Reaction (LCR), Transcription Mediated Amplification (TMA); Self-Sustaining Sequence Replication (3SR), Rolling Circle Amplification (RCA), Nucleic Acid Sequence Based Amplification (NASBA), Q β replicase system, Helicase Dependant Amplification, Loop Mediated Amplification (LAMP) and SMart Amplification (SMAP). The skilled artisan will further appreciate that the types of molecular assays in which the specimen processing controls of the invention can be employed include assays that employ homogeneous, "real-time" detection by measurement of fluorescence or other means such as real-time PCR or real-time SDA.

FIG. 2c displays another embodiment of a use of a molecular assay control, e.g., SPC, in connection with a molecular assay. Specifically, FIG. 2c illustrates another embodiment of use of a molecular assay control, i.e., SPC, in connection with the BD MAX platform or other molecular diagnostic systems in which no nucleic acid capture is performed. Steps of this assay are divided into manually performed steps and automated steps. These steps are further categorized as relating to sample preparation, sample processing, amplification, and detection. In some embodiments, sample preparation steps are manually performed, and, sample processing, amplification, and detection steps are automatically performed. A person skilled in the art will recognize that the steps of a molecular assay can vary, and that the division of steps of a molecular assay can likewise vary.

Similar to embodiments shown in FIGS. 2a and 2b, some embodiments of sample preparation steps, as depicted in FIG. 2c, comprise specimen collection, specimen transport and storage, and pre-processing of the specimen. In some embodiments of sample preparation steps, pre-processing of the specimen may be performed, while other embodiments of sample preparation steps exclude pre-processing of the specimen.

Sample processing steps of some embodiments of a molecular assay, as depicted in 2c, comprise mixing of the sample with the lysis enzyme and/or chemical agent(s) and the control, i.e., SPC, cell lysis, and inactivation of the lysis reagent. In some embodiments, the lysis reagent can be inactivated through the use of heat or temperature change, while other embodiments may involve the inactivation of the lysis reagent through change in pH or other characteristic of the reagent solution. In other embodiments in which the presence of active lysis reagent does not result in inhibition of downstream processes such as nucleic acid amplification or detection, the step of lysis reagent inactivation can be omitted.

Amplification steps of some embodiments of a molecular assay, as depicted in 2c, comprise mixing lysate with amplification reagents, target denaturation, primer and probe hybridization, and amplification. Finally, detection steps of specific embodiments of a molecular assay, as depicted in FIG. 2c, can comprise, for example, homogeneous real-time fluorescent detection. As discussed above, however, the skilled artisan will readily appreciate that the embodiments disclosed herein are useful in the control of various types of molecular assays, including assays that do not require nucleic acid amplification, and including various nucleic acid amplification techniques known by those skilled in the art.

Additionally, as depicted in FIGS. 2a through 2c, a control, e.g., SPC, can be used to monitor all, or portions of, the molecular assay. FIG. 2a depicts one embodiment of use of the control, i.e., SPC, in which the control, i.e., SPC, is contained within the specimen transport device. In this embodiment, the control, i.e., SPC, monitors all of the automated steps of the molecular assay, including the lysis, extraction, amplification, and detection steps. In some embodiments of a method of use of a control, i.e., SPC, in connection with a molecular assay, and as depicted in FIG. 2a, the control, i.e., SPC, also monitors the specimen transport, specimen storage, and any specimen pre-processing steps. In one embodiment, the control, i.e., SPC, can be provided in stable dried form in the specimen transport device and rehydrated with the specimen. In another embodiment, the control, i.e., SPC, can be added to the specimen in either liquid or dried form at the time of specimen collection. In both these embodiments, successful detection of the control, i.e., SPC, would indicate that that all steps in the process were performed correctly, including shipment and storage of the specimen within the specified parameters of temperature and time prior to nucleic acid extraction, amplification and detection. Conversely, failure to detect the control, i.e., SPC, would indicate failure in one or more process steps.

FIG. 2b depicts an embodiment of a method of use of a control, i.e., SPC, in connection with a molecular assay in which a control, i.e., SPC, is dried with the extraction reagents. In some embodiments, and as depicted in FIG. 2b, the extraction reagents include magnetic affinity beads for capture of nucleic acid and a lysis enzyme. In some embodiments, and as depicted in FIG. 2b, the control, i.e., SPC, dried with the extraction reagents is rehydrated with the sample, and thus monitors the efficacy of all of the automated molecular assay steps including the extraction, amplification, and detection steps.

FIG. 2c depicts another embodiment of a method of use of a control, i.e., SPC, in connection with a molecular assay in which a control, i.e., SPC, is dried with the lysis enzyme. In this embodiment, the control, i.e., SPC, is rehydrated with the sample, and is thus able to monitor the efficacy of all of the automated molecular assay steps, including the sample processing, amplification, and detection steps.

Verification of the results of NAAT and other testing is performed, in some embodiments, with a control, i.e., SPC. In some embodiments, the control, i.e., SPC, monitors steps of the testing process and demonstrates successful completion of the various steps of that assay process. Embodiments of controls, i.e., SPC, include internal, external, full process, and partial process controls. Some variations of full process controls created for use in connection with processes that utilize mechanical force for cell lysis use B. atropheus subsp. globigii ("B. globigii") spores as specimen process controls. As discussed elsewhere herein, however, testing indicates that *B. globigii* spores are unsuitable for use in connection with embodiments of molecular assays that employ enzyme mediated lysis, e.g., by ACP-dependent lysis. FIG. 3 depicts the results of a comparison of treatments to lyse *B. globigii* spores, in which exposure to ACP for 20 min at 37° C. is compared to mechanical lysis with glass beads and to a control, i.e., SPC, that lacks ACP. As shown in FIG. 3, the results of the attempted lysis of *B. globigii* spores with ACP are comparable to those from the untreated control, i.e., SPC, sample, indicating failure of the ACP to induce lysis. In contrast, mechanical lysis with glass beads was shown to be highly efficient and reproducible. These results demonstrate that because ACP is not efficacious in lysing *B. globigii* spores, the spores are not a suitable control, i.e., SPC, for monitoring ACP-dependent lysis in connection with a molecular assay.

In contrast to the discovered traits of *B. globigii*, some embodiments of a control, i.e., SPC, usable in connection with present methods of a molecular assay are susceptible to enzyme mediated lysis, e.g., ACP-driven lysis. The skilled artisan will appreciate that the embodiments disclosed herein are useful in connection with controlling cell lysis mediated by other enzymes known in the art, including but not limited to lysozyme, lysostaphin, zymolase, cellulase, mutanolysin, glycanases, proteases including proteinase K and the like, either alone or in combination with ACP. In some embodiments of a control, i.e., SPC, for use with a molecular assay utilizing ACP, the control, i.e., SPC, is designed to maintain its integrity prior to lysis and throughout the reagent preparation or manufacturing process. In further embodiments of a control, i.e., SPC, for a molecular assay utilizing ACP, the control, i.e., SPC, is designed to retain its susceptibility to ACP.

In some embodiments, the molecular assay control, i.e., SPC, disclosed herein can comprise bacterial cells, e.g., Gram positive or Gram negative bacterial cells, or a combination thereof. In some embodiments, the SPC can comprise Gram positive cells can include cells that are from one or ore of the following genera of bacteria: *Bacillus, Listeria, Clostridium, Staphylococcus, Enterococcus, Streptococcus*, and the like. For example, in some preferred embodiments, the SPC can comprise *Bacillus* cells, e.g., *B. subtilus, B. globigii, B. cereus*, or the like. In some embodiments, the SPC can include vegetative cells of *Bacillus* species, i.e., vegetative *Bacillus subtilis* ("*B. subtilis*") cells, vegetative *B. globigii* cells, vegetative *B. cereus* cells, or the like. More particularly, preferred embodiments of a molecular assay control, i.e., SPC, further comprise vegetative cells of recombinant *B. subtilis* containing a cloned target sequence that is stably integrated into the host chromosome or carried on an episomal plasmid, bacteriophage, or the like. Thus, in some embodiments of a molecular assay control, i.e., SPC, a cell may contain an assay-specific nucleic acid sequence that is integrated in a stable fashion into the host chromosome.

In some embodiments, the SPC can be fixed. For example, in embodiments wherein cells of *Bacillus* are used as an SPC, the cells may be prepared in such a way so as to minimize the presence of spores and/or to synchronize bacterial replication to generate a morphologically homogeneous population at the time of harvest during vegetative cell growth, e.g., mid-late log-phase. As discussed herein, by synchronizing cell growth and fixing the cells, one can advantageously ensure that the culture is essentially free of contaminating extracellular DNA. Accordingly, in some embodiments, provided is a control, i.e., SPC, for a molecular assay comprising fixed *B. subtilis* cells to prevent further growth or maturation, changes in the morphology of the cells, and sporulation.

EXAMPLE 1

*Bacillus* Spores as Specimen Process Controls for ACP-Mediated Cell Lysis

The following experiments were performed in order to determine whether *Bacillus* spores were suitable for full process controls in assays utilizing enzymatic cell lysis agents, such as ACP. Two experiments were performed on different lots of *B. subtilis* spores. In the chart labeled Lot 1 of FIG. 4, *B. subtilis* spores were exposed to the 5 different cell lysis conditions listed in Table 1, below.

TABLE 1

Comparison of ACP-dependent lysis between lots of *B. subtilis* spores (refer to FIG. 4)

| Experimental Group | Conditions |
|---|---|
| ACP 20 | Treatment of *B. subtilis* spores for 20 min at 37° C. in the presence of ACP, followed by 5 min at 99° C. to inactivate the enzyme |
| ACP 10 | Treatment of *B. subtilis* spores for 10 min at 37° C. in the presence of ACP, followed by 5 min at 99° C. to inactivate the enzyme |
| ACP TE | Incubation of ACP for 20 min at 37° C., followed by 5 min at 99° C. to inactivate the enzyme (no spores present) |
| Beads | Mechanical glass bead lysis of *B. subtilis* spores followed by 2 min at 95° C. |
| Heat | Heat treatment of *B. subtilis* spores for 5 min at 99° C. without ACP |
| NT | No target/Control (no spores present) |

Following lysis, the samples were subjected to nucleic acid amplification and detection reactions, using real-time PCR and fluorescent detection of target nucleic acid sequences. Amplification and detection was reported in terms of SDPA (Second Derivative Peak Abscissa—the point of maximum acceleration of the fluorescent curve). The results are shown in FIG. 4. Samples in which no reaction was observed were assigned an SDPA value of zero. Lower SDPA values are and indicative of more efficient amplification and correlate with the presence of higher concentrations of target DNA.

No amplification was obtained in the ACP TE, Heat, and No Target/Control groups, indicating the absence of free *B. subtilis* DNA and, in the case of the Heat group, failure to lyse the spores. Additionally, both the group subject to lysis by Beads and the ACP 20 group yielded similar results ($\Delta$SDPA=0.6; p=0.492) indicating the presence of equivalent quantities of detectable free DNA as a result of spore lysis. However, in contrast to these results, Lot 2 spores yielded different degrees of lysis between the ACP 10, ACP 20, and Beads groups (FIG. 4). In contrast to testing with Lot 1 spores, the efficiency of lysis in the Lot 2 ACP 20 group was lower than that for the Lot 2 Bead group as determined by the difference in SDPA values ($\Delta$SDPA=3.7; p<0.001). In another surprising difference, whereas the Lot 1 spores yielded no detectable lysis for the Heat group, the chart for Lot 2 indicates detectable lysis in some samples treated under this condition. As shown in FIG. 4, different experiments to test the susceptibility of *B. subtilis* spores to ACP-dependent lysis yielded inconsistent results. Viewed in total, therefore, lysis of *B. subtilis* spores by ACP has not been shown to be reproducible. As such, some embodiments of a control, i.e., SPC, for use with a molecular assay comprising *B. subtilis* can instead comprise *B. subtilis* cells fixed in vegetative growth.

Fixation of vegetative cells prevents further growth or maturation and changes in morphology and, in the case of *B. subtilis*, potential sporulation. Fixation therefore helps ensure the homogeneity of the overall cell population, thus increasing the lot-to-lot consistency of the composition of the control, i.e., SPC, as well as increasing the consistency of the assay results. In addition to stabilizing the development of the cells, fixation relatively decreases the likelihood of cell lysis during cell manipulation when compared to use of non-fixed cells. As a result, because fixed cells are inherently more lyse-resistant, they can more readily be stored for extended periods. Thus, fixed cells are less impacted by downstream manufacturing processes, such as, for example, washing to remove extracellular DNA, dilution to the appropriate target concentration, formulation with other assay components, and drying for long-term storage.

EXAMPLE 2

Fixed *Bacillus* Cells in Vegetative Growth Phase as Specimen Process Controls

The following experiments were performed to test whether vegetatively-growing *Bacillus* cells can be used for specimen process controls.

Some preferred embodiments of a control, i.e., SPC, for a molecular assay can comprise formalin fixed *B. subtilis* cells. FIG. 5 shows a comparison of three groups, each having a component exposed at 37° C. to a solution of ACP in 1× Tris-EDTA ("TE") for 30 min, and a component not exposed to ACP. These groups are, a first group comprising unfixed *B. subtilis* cells, a second group comprising formaldehyde fixed *B. subtilis* cells, and a third group comprising gluteraldehyde fixed *B. subtilis* cells. As shown in FIG. 5, the components of the non-fixed *B. subtilis* group are not distinguishable as the component exposed to the ACP solution and the component not exposed to ACP solution both produce a similar result (p=0.33), indicating that the quantity of extracellular DNA present was similar in these samples. In contrast, with the formalin-fixed *B. subtilis* cells there is a clear distinction between the results of the ACP-treated and untreated groups. To a lesser degree than for the formalin-fixed group, with the gluteraldehyde-fixed *B. subtilis* cells one can easily discriminate between ACP-treated and untreated groups. Thus, the data indicate that unfixed cells are not ideal for use as a control, e.g., SPC, for lysis. In contrast, for the cells fixed with either formaldehyde or gluteraldehyde, there was a statistically significant difference in SDPA values between the ACP-treated and untreated groups. Cells treated with ACP yielded lower SDPA values compared with the untreated cells, thereby demonstrating ACP-dependent lysis and the applicability of fixed cells as controls, e.g., SPC, for lysis by this method.

As discussed above, the inability to distinguish between treated and untreated cells in the case of unfixed *B. subtilis* results from the sensitivity of the cells to lysis, which hampers removal of extracellular DNA and other sample impurities. It was therefore surprisingly discovered that fixation of the control cells during vegetative growth enables use of *B. subtilis* cells as a molecular assay control to monitor the efficacy of cell lysis.

EXAMPLE 3

Susceptibility of Fixed Vegetative Cells of *B. subtilis* to ACP

The susceptibility of fixed vegetative cells of *B. subtilis* to ACP was further illustrated by an experiment in which samples were tested under six experimental conditions, as outlined in Table 2, below:

TABLE 2

Treatment groups used to test formalin-fixed *B. subtilis* cells

| Treatment Group | Conditions* |
|---|---|
| 1/20 + ACP | Cells diluted 1/20 and incubated with ACP |
| 1/20 Inactive ACP | Cells diluted 1/20 and incubated with heat-inactivated ACP |

TABLE 2-continued

Treatment groups used to test formalin-fixed *B. subtilis* cells

| Treatment Group | Conditions* |
| --- | --- |
| 1/20 w/o ACP | Cells diluted 1/20 and incubated without ACP |
| 1/200 + ACP | Cells diluted 1/200 and incubated with ACP |
| 1/200 Inactive ACP | Cells diluted 1/200 and incubated with heat-inactivated ACP |
| 1/200 w/o ACP | Cells diluted 1/200 and incubated without ACP |

*All incubations employed fixed *B. subtilis* cells and were performed for 20 min at 37° C., followed by 5 min at 99° C.

Three groups were exposed to ACP and three control groups were not exposed to ACP treatment. Following lysis, samples were subjected to amplification and detection reactions using real-time PCR with fluorescent detection of target nucleic acid sequences. The results are shown in FIG. 6. Irrespective of the dilution of cells used (either 1/20 or 1/200), there was approximately a mean ΔSDPA of 10 between the ACP-treated group and the groups exposed to heat-inactivated ACP or no ACP ($p<0.001$). These results serve to confirm that formaldehyde-fixed *B. subtilis* cells are susceptible to ACP and that it is possible to obtain adequate discrimination between ACP-treated and untreated conditions to enable use of such cells as controls for ACP-dependent cell lysis.

Due to the tendency of non-fixed cells to lyse, large quantities of extra-cellular DNA can remain associated with non-fixed cells, even after washing. This extra-cellular DNA prevents accurate determination of ACP dependent lysis. In contrast, when employing embodiments comprising fixation, the fixed cells can undergo several rounds of washing post-fixation, without undesired lysing. These washings remove most extracellular DNA and allow clear differentiation between ACP-treated and untreated cells.

Controls, i.e., SPC, that employ *B. globigii* spores require complicated and time-consuming preparation methods. US2007/0015139 describes a process for production of *B. globigii* spores that includes a ten day maturation period and purification through a sucrose gradient in order create a homogenous population that is free of contaminating vegetative cells. In some embodiments comprising vegetative cells, *B. subtilis* can be grown to a pre-determined optical density in early-, mid-, or late-exponential phase in approximately two to eight hours, at which time the cells can be harvested and fixed. Embodiments of a control, i.e., SPC, for use with a molecular assay comprising mature, fixed, vegetative *B. subtilis* cells can be stable for extended time periods at a broad range of temperatures. Advantageously, this long term stability enables storage of these cells without degrading their susceptibility to ACP-driven lysis.

In one preferred embodiment, formalin-fixed vegetative cells of recombinant *B. subtilis* can be prepared with an assay specific control sequence that is integrated in a stable fashion into the host chromosome, while in other embodiments the control sequence can be present on a plasmid, bacteriophage, or the like. In another preferred embodiment, the control cells i.e., SPC cells, can be dried with other sample processing reagents such as nucleic acid binding particles, e.g., derivatized or underivatized beads such as magnetic beads, used in the recovery of nucleic acid and enzymes or chemical agents used for cell lysis. Other exemplary sample processing reagents that may be present in a preferred embodiment include excipients such as trehalose, dextran, polyethylene glycol or polyvinyl pyrrolidone, buffer constituents for stabilization and/or enzyme activity, enzyme inhibitors, enzyme cofactors, chelating agents, oligonucleotides, fluorescently labeled probes, ionic or nonionic detergents, chaotropes, carrier molecules such as bovine serum albumin or salmon sperm DNA, and antifoaming agents. The combination of the control cells, i.e. SPC cells, and the sample processing reagents can be, in some embodiments, reconstituted using the specimen matrix and other extraction reagents. In some embodiments, extraction reagents can include a detergent and a buffer. In some embodiments, the buffer can comprise a combination of Tris and EDTA, known as TE, or other similar buffer. Some embodiments can also use Triton-X 100, Tween 20 or other similar detergent. The control cells, i.e., SPC cells, and the specimen cells, can be mixed with the extraction reagents as discussed elsewhere herein to lyse the cells and release nucleic acids.

In some embodiments, nucleic acids from the *B. subtilis* cells and target nucleic acids, if present, from the specimen cells can be captured. In some embodiments, nucleic acids from the control cells, i.e., SPC cells, and from the specimen cells can be captured on the surface of magnetic affinity beads. Examples of binding particles, such as derivatized beads useful for the capture and elution of nucleic acids from solution can be found, for example, in U.S. Patent Application Publication No. 2006/0166233, U.S. Patent Application Publication No. 2009/0131650, and the like. The skilled artisan will appreciate that many different types of nucleic acid binding particles known to those skilled in the art can advantageously be used in connection with the embodiments disclosed herein. In embodiments employing derivatized magnetic nucleic acid affinity beads, the magnetic affinity beads of some embodiments can be positively charged. The magnetic affinity beads can be introduced into the process at different points in different embodiments. In some embodiments, magnetic affinity beads may be introduced during the cell lysis phase. In other embodiments, the magnetic affinity beads may be introduced into the process during the extraction phase. In some embodiments, the magnetic affinity beads can be introduced into the process with the extraction solution.

In some embodiments, the process can include the step of washing the magnetic affinity beads bound by nucleic acids with a wash buffer and/or a detergent. In some embodiments, the buffer can comprise Tris, or other similar buffer. Some embodiments also use Triton-X 100, Tween 20 or other similar detergent. After washing to remove inhibitors, some embodiments recover the nucleic acids from the magnetic affinity beads. In some embodiments, the DNA can be recovered from the magnetic affinity beads through use of an elution buffer. In some embodiments, the elution buffer can have a different pH than that of the wash solution. In other embodiments, the elution buffer used to recover nucleic acids from the magnetic affinity beads can comprise a release solution. In some preferred embodiments, the release solution can have a high pH, and may comprise a sodium hydroxide solution or other similar strong alkaline solution. In other embodiments, the release solution can have a pH of 9 or greater, e.g., pH 10, 11 or 12 or greater.

In some embodiments of a method of control of a molecular assay, the pH of the combination of the elution buffer containing the released nucleic acids can be lowered by addition of a neutralization buffer. In some embodiments of a method of control of a molecular assay, the pH of the elution buffer containing the released nucleic acids can be lowered to a level that is compatible with subsequent analysis steps. In some embodiments, the pH can be lowered to a level compatible with subsequent nucleic acid amplification, e.g., PCR or the like. In other embodiments, the pH can be lowered to a level that is compatible with subsequent amplification and/or detection processes.

The elution buffer containing the released nucleic acids can then be mixed, in some embodiments, with reagents for further processes. In embodiments, the neutralized elution buffer containing the released DNA can be used to reconstitute dried reagents, such as reagents used in nucleic acid amplification and/or detection assays. In further embodiments in which PCR analysis is performed, the control nucleic acids, i.e., SPC nucleic acids, can be co-amplified and detected with any of the target nucleic acids that is present.

Embodiments of methods of preparation of a control, i.e., SPC, for molecular assays use a broad range of fixed and unfixed cells. A person skilled in the art will recognize that embodiments of methods of preparation of a control, i.e., SPC, for use with a molecular assay use different modes of fixation that encompass a broad range of fixing techniques. Some embodiments for preparation of a control, i.e., SPC, for use with a molecular assay use covalent fixation, which causes covalent cross-linking of cell surface proteins. Covalent fixation can be accomplished, for example, using a solution of formalin, paraformaldehyde, or gluteraldehyde, or combinations thereof. Other embodiments for preparation of a control, i.e., SPC, for use with molecular assays use non-covalent fixation. Non-covalent fixation can be conducted with a mixture of alcohols such as methanol or ethanol to induce protein denaturation and precipitation. However, a person skilled in the art will recognize that a wide variety of methods of fixation may be used in connection with designing and preparing a control, i.e., SPC, for use in connection with a molecular assay, including fixation through use of oxidizing agents such as osmium tetraoxide and potassium permanganate, both of which can cross-link a broad range of cellular constituents, or other methods. As a variety of fixation agents can be properly used in connection with methods of preparing a control, i.e., SPC, for a molecular assay, a person skilled in the art will recognize that selection of a single fixative will include consideration of the relative susceptibility of the control cells, i.e., SPC cells, to lysis in the fixed state as compared to the susceptibility to lysis of the target analyte.

In one embodiment, for example, vegetative cells of *B. subtilis* can be grown, harvested, and fixed. In one embodiment, for example, vegetative cells of *B. subtilis* can be grown to exponential phase, harvested by centrifugation, washed with HEPES buffer and then fixed by resuspending in neutral buffered formalin. In some aspects, the formalin can be, for example, 25% formaldehyde, 9% formaldehyde, 6% formaldehyde, 3% formaldehyde, 1% formaldehyde, or any other desired concentration of formaldehyde. In some embodiments, fixation can be performed, for example, by incubating the cell suspension at 2-8° C., a 1-20° C., and −10-50° C., or within any other desired temperature range overnight, for at least 12 hours, for at least 8 hours, for at least 4 hours, for at least 2 hours, for at least 1 hour, for at least 30 minutes, or for any other desired time.

After fixation, the cells can be harvested. In some embodiments, the cells can be harvested by, for example centrifugation and can be washed. In some embodiments, the cells can be washed by resuspending the cells in a large excess of 1 mM HEPES buffer (4-(2-hydroxyethyl)-1-piperazineethanesulfonic acid), 10 mM HEPES buffer, 25 mM HEPES buffer, 50 mM HEPES buffer, 100 mM HEPES buffer or any other desired HEPES buffer concentration of desired buffer. In some embodiments, the washing can further comprise recentrifugation. In some embodiments, the volume of wash buffer represents, for example, at least 10× the volume of the cells, 50× the volume of the cells, at least 200× the volume of the cells, or at least 1000× the volume of the cells. Washing of the cells to remove the fixative and extracellular DNA can be performed at least once, at least twice, at least three times, at least five times, at least 10 times, or any other desired number of times. In some embodiments, the fixed cells can then be resuspended in a small volume of wash buffer or other suitable storage medium.

In some embodiments, the method of preparing an SPC may be judged based on certain criteria. In some embodiments, these criteria can include a variety of factors, some of which are listed in Table 3 below. A person of skill in the art will recognize that the criteria depicted in Table 3 are not comprehensive, and that such criteria, as well as others could be used to select a method of preparing an SPC. A person of skill in the art will further recognize that while Table 3 includes some criteria with certain associated benefits, these results should not be construed as requiring the use of, or excluding the potential use of any of the above-listed or otherwise known criteria for selecting a method of preparing an SPC.

TABLE 3

Examples of manufacturing process requirements

| Attribute | Comment |
| --- | --- |
| Maintenance of Bacterial Integrity | Enables the SPC to monitor for cell lysis |
| Compatibility with Lysis Technology | In some embodiments the formulation of the SPC does not be inhibitory to the lysis method: e.g., excipients used in the drying process do not inhibit ACP activity |
| Compatibility with DNA Extraction Technology | In some embodiments the formulation of the SPC does not be interfere with the recovery of DNA from the test sample: e.g., excipients used in the drying process do not compete with DNA for binding to the magnetic affinity beads or other solid phase matrix used for DNA recovery |
| Compatibility with DNA Nucleic Acid Amplification Technology | In some embodiments the formulation of the SPC does not be interfere with amplification and detection of DNA: e.g., excipients used in the drying process do not be inhibitory to PCR or other amplification technology |
| Rehydration Efficiency | In some embodiments the SPC provided in dried form that is designed to dissolve within a specified time frame that is compatible with the throughput of the assay system: e.g., ≤1 min or ≤5 min |
| Reagent Stability | In some embodiments the manufacturing process yields a product that is stable over time as defined by the maintenance of bacterial integrity and solubility |

TABLE 3-continued

Examples of manufacturing process requirements

| Attribute | Comment |
| --- | --- |
| Manufacturability Scaleability Environmental requirements | In some embodiments the manufacturing process is flexible to allow for production of different quantities of controls with minimal change in workflow or equipment, and in some embodiments the environmental requirements such as control of ambient temperature or humidity are minimal. Advantageously this can decrease the cost of the test. |
| Cost Per Test | In some embodiments cost per test should be as low as possible. Advantageously this can facilitate widespread use of the test. |

Figure 7:
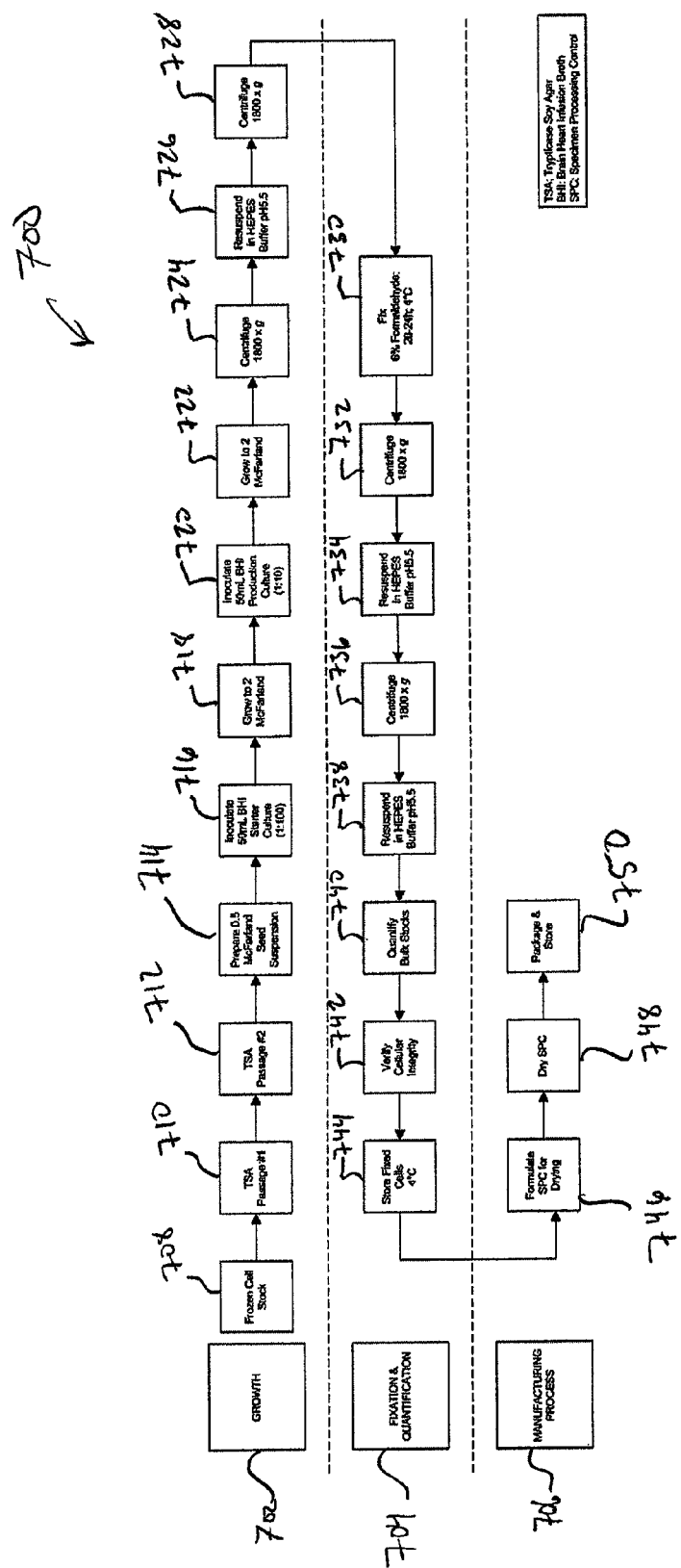
FIG. 7 is a flow-chart illustrating one embodiment of a process of one method of preparing a SPC based on fixed cells.

FIG. 7 depicts a process 700 of one method of preparing a SPC based on fixed cells. In some embodiments, the fixed cells can comprise, for example, B. subtilis cells. The process 700 is divided into three phases describing the general process in each phase. The first phase, depicted in block 702 is the growth phase. The second phase, depicted in block 704 is the fixation and quantification phase. The third phase, depicted in block 706, is the manufacturing phase. The process 700 begins in the first phase 702, proceeds to the second phase 704, and terminates in the third phase 706.

Specifically, the process 700 begins in the first phase 702 at block 708 upon receipt of the cell stock. In some embodiments, the cell stock can comprise pre-prepared cells of a specific type, culture, or preparation. In some embodiments, the cell stock can be in any form facilitating storage, including in frozen form.

After the cell stock is received in block 708, the process 700 advances to block 710 and performs the first passage. In some embodiments, the first passage can be initiated by transferring some of the cells from the frozen cell stock to a fresh growth medium. In some embodiments, the fresh growth medium can comprise a liquid or gel that is configured to support the growth of the cells. In some embodiments, a variety of growth media can be used to support the growth of the cells. In some embodiments, for example, the growth medium can comprise trypticase soy agar, eosin methylene blue agar, MacConkey agar, mannitol salt agar, xylose lysine desoxyschlolate, or any other desired growth medium. In some embodiments attributes of the growth medium can be configured to correspond to cell attributes, thus, in some embodiments, Gram-negative cells can be used with growth media configured to support Gram-negative cells, and Gram positive cells can be used with growth media configured to support Gram-positive cells.

In some embodiments, the first passage can be performed for a desired duration and in desired environmental conditions. In some embodiments, the duration and the specific environmental conditions can depend on characteristic of the cell being passaged, including, for example, its ideal environment, its required time to replicate, and/or any other attribute.

After the process 700 performs the first passage as depicted in block 710, the process 700 performs the second passage in block 712. Similar to the first passage, the second passage can be initiated by transferring some cells to a fresh growth medium, and specifically by transferring some cells from the first passage to a fresh growth medium. As also discussed above, the growth medium can be selected based on the cells that are being passaged, and the duration of the passaging and the environmental conditions can be controlled based on the cells that are being passaged. In some embodiments, the process 700 can comprise the second passage as depicted in block 712, and in some embodiments, the process 700 does not include the second passage. In some embodiments, the process 700 passaging in addition to the first and second passages as depicted in blocks 710 and 712. In some embodiments, the number of passages performed on the cells can be based on the desired purity of the cells, the duration of time that the cells hade been stored, or any other factor.

After the process 700 completes the second passage, the process 700 moves to block 714 and prepares a seed suspension. In some embodiments, the seed suspension can comprise a mixture of the cells and a suspending liquid. In some embodiments, the suspending liquid can comprise, for example, water or any other desired liquid. In some embodiments, the liquid can be pure, or can be fortified with nutrient and other chemicals, biologicals, or any composition configured to sustain the life of the cells. The seed suspension can comprise any desired turbidity, and thus the concentration of the cells in the suspension can vary. In some embodiments, the suspension can comprise a 0.001 McFarland standard suspension, a 0.01 McFarland standard suspension, a 0.1 McFarland standard suspension, a 0.5 McFarland standard suspension, or any other desired suspension.

After the process prepares the seed suspension at block 714, the process 700 proceeds to block 716 and inoculates the suspension. In some embodiments, the inoculation can comprise nutrients to sustain the life of the cells and to encourage growth of the cells. The nutrients in the inoculation can comprise a variety of items, including, for example, brain heart infusion broth ("BHI"), lysogeny broth (LB), super optimal broth (SOC medium), or any other desired nutrients. In some embodiments, the inoculation can comprise a range of volumes and concentrations, which volume and concentration can be based on the number of cells that require nutrition and the duration of time for which the inoculation should support the cells. In some embodiments, the inoculation can comprise 1 mL, 10 mL, 20 mL, 50 mL, 100 mL, 200 mL, 500 mL, or any other desired volume. In some embodiments the inoculum volume can represent $\frac{1}{10}^{th}$, $\frac{1}{100}^{th}$ or $\frac{1}{1000}^{th}$ the volume of the starter culture or any other desired volume In some embodiments, the inoculation can comprise 0.5 mL seed suspension in 50 mL of a BHI medium.

After the process 700 inoculates the suspension as depicted in block 716, the process 700 advances to block 718 and allows the culture to grow. In some embodiments, the duration of time allowed for the culture to grow, and the environmental conditions can be varied based on the desired number of cells, the type of cells, or any other factor. In some embodiments, the culture is allowed to grow until the concentration of cells in the culture reaches a predetermined threshold. In some embodiments, the number of cells in the culture can be determined based on the turbidity of the culture. In some embodiments, for example, the culture is allowed to grow until the turbidity of the culture exceeds some threshold value. Specifically, the culture may be allowed to grow until the culture suspension comprises a 0.01 McFarland standard suspension, a 0.1 McFarland standard suspension, a 0.5 McFarland standard suspension, a 1 McFarland standard suspension, a 2 McFarland standard suspension, a 4 McFarland standard suspension or any other desired suspension.

After the culture is allowed to grow, as depicted in block 718, the process proceeds to block 720 and inoculation of the production culture. In some embodiments, the inoculation can comprise nutrients to sustain the life of the cells and to encourage growth of the cells. The nutrients in the inoculum can comprise a variety of items, including, for example, brain heart infusion broth ("BHI"), lysogeny broth (LB), super optimal broth (SOC medium), or any other desired nutrients. In some embodiments, the inoculum can comprise a range of volumes and concentrations. In some embodiments, the inoculum of block 720 can comprise the same or different nutrients, volume, and concentration as the inoculum of block 716. In some embodiments, the inoculum can comprise 1 mL, 10 mL, 20 mL, 50 mL, 100 mL, 200 mL, 500 mL, or any other desired volume of the starter culture. In some embodiments the inoculum represents $\frac{1}{10}^{th}$, $\frac{1}{100}^{th}$ or $\frac{1}{1000}^{th}$ the volume of the production culture or any other desired volume. In some embodiments, the inoculation can comprise 5 mL bacterial suspension into a production culture of 50 mL of a BHI medium.

After the process 700 inoculates the suspension as depicted in block 720, the process 700 advances to block 722 and allows the culture to grow. In some embodiments, the duration of time allowed for the culture to grown, and the environmental conditions can be varied based on the desired number of cells, they type of cells, or any other factor. In some embodiments, the culture is allowed to grow until the concentration of cells in the culture reaches a predetermined threshold. In some embodiments, the number of cells in the culture can be determined based on the turbidity of the culture. In some embodiments, for example, the culture is allowed to grow until the turbidity of the culture exceeds some threshold value. Specifically, the culture may be allowed to grow until the culture suspension comprises a 0.01 McFarland standard suspension, a 0.1 McFarland standard suspension, a 0.5 McFarland standard suspension, a 1 McFarland standard suspension, a 2 McFarland standard suspension, a 4 McFarland standard suspension or any other desired suspension.

After the culture is allowed to grow as depicted in block 722, the process 700 moves to block 724 and the cells are harvested. In some embodiments, the cells can be harvested using any desired filtration technique, separation technique, or other harvesting technique. In some embodiments, the cells can be harvested, for example, by separation performed with a centrifuge. In some embodiments, a centrifuge can be used to separate the cells from the suspending liquid by applying a g-load to the suspension for a duration of time. In some embodiments, for example, a g-load of 100 g's, 500 g's, 1000 g's, 1500 g's, 1800 g's, 2500 g's, 5000 g's, or any other desired g-load can be applied to the suspension. In some embodiments, the g-load can be applied to the suspension for, for example, 10 seconds, 30 seconds, 1 minute, 2 minutes, 5 minutes, 10 minutes, 30 minutes, 60 minutes, 2 hours, 5 hours, 10 hours, or any other desired duration of time.

After the cells have been harvested as depicted in block 724, the process 700 moves to block 726 and resuspends the cells. In some embodiments, the resuspension of the cells can be configured to wash the cells to purify the sample. Thus, in some embodiments, the washing of the sample can remove impurities from the sample such as, for example, extracellular DNA, lysed cell parts, or any other impurity. In some embodiments, the washing can include the step of resuspending the cells in a buffer. In some embodiments, the buffer can comprise any desired buffer, including, for example, an MES buffer, an ADA buffer, a PIPES buffer, an ACES buffer, a BES buffer, and TES buffer, a HEPES buffer, a tricine buffer, a bicine buffer, a TAPS buffer, a TRIS buffer, an SSC buffer, or any other desired buffer. In some embodiments, the buffer can be configured to have a desired pH and/or concentration. In some embodiments, the desired pH can comprise any pH configured to achieve a desired result. In one specific embodiment, the cells can be resuspended in HEPES buffer solution having a pH of approximately 5.5 and a concentration of 50 mM.

After the cells are resuspended in block 726, the process 700 moves to block 728 and the cells are harvested. In some embodiments, the cells can be harvested using any desired filtration technique, separation technique, or other harvesting technique. In some embodiments, the cells can be harvested, for example, by separation performed with a centrifuge. In some embodiments, a centrifuge can be used to separate the cells from the suspending liquid by applying a g-load to the suspension for a duration of time. In some embodiments, for example, a g-load of 100 g's, 500 g's, 1000 g's, 1500 g's, 1800 g's, 2500 g's, 5000 g's, or any other desired g-load can be applied to the suspension. In some embodiments, the g-load can be applied to the suspension for, for example, 10 seconds, 30 seconds, 1 minute, 2 minutes, 5 minutes, 10 minutes, 30 minutes, 60 minutes, 2 hours, 5 hours, 10 hours, or any other desired duration of time.

In some embodiments, the resuspension and harvesting of the cells can be repeated more or fewer times than shown in FIG. 7. Thus, in some embodiments, the process 700 may not include blocks 726 and 728, or may repeat block 726 and 728 two times, five times, ten times, or any other desired number of times.

After the cells are harvested in block 728, the process 700 moves to block 730 and fixes the cells. In some embodiments, a variety of techniques can be used to fix the cells. In some embodiments, and as discussed above, a wide variety of methods of fixation may be used to fix the cells, including, for example, fixation through use of oxidizing agents such as osmium tetraoxide and potassium permanganate, fixation through gluteraldehyde or formaldehyde, or any other fixation technique. In some embodiment, the duration of the cell fixation and the environmental parameters may vary based on the type of cell being fixed, the fixation technique, and the degree to which the cells are being fixed. In some embodiments in which *B. subtilis* cells are being fixed for use as a process control, the *B. subtilis* cells are fixed with a 1%, 2%, 5%, 6% 10%, 20%, 25%, or any other concentration formaldehyde solution, for between 20-24 hours, 15-30 hours, 10-40 hours, 1-50 hours, or for any other duration, and at 1° C., 2° C., 5° C., 10° C., 20° C., 25° C., 50° C., 100° C., or any other desired temperature.

After the cells are fixed in block 730, the process 700 moves to block 722 and the cells are harvested. In some embodiments, the cells can be harvested using any desired filtration technique, separation technique, or other harvesting technique. In some embodiments, the cells can be harvested, for example, by separation performed with a centrifuge. In some embodiments, a centrifuge can be used to separate the cells from the suspending liquid by applying a g-load to the suspension for a duration of time. In some embodiments, for example, a g-load of 100 g's, 500 g's, 1000 g's, 1500 g's, 1800 g's, 2500 g's, 5000 g's, or any other desired g-load can be applied to the suspension. In some embodiments, the g-load can be applied to the suspension for, for example, 10 seconds, 30 seconds, 1 minute, 2 minutes, 5 minutes, 10 minutes, 30 minutes, 60 minutes, 2 hours, 5 hours, 10 hours, or any other desired duration of time.

After the cells have been harvested as depicted in block 732, the process 700 moves to block 734 and resuspends the cells, to block 736 and harvest the cells, and to block 738 and resuspends the cells. The combination of these steps can, as discussed above, increase the purity of the sample by washing impurities, such as extracellular DNA from the sample. As also discussed above, all or a portion of these steps can be included in a process. As also discussed above, some or all of these steps can be repeated.

Figure 8:
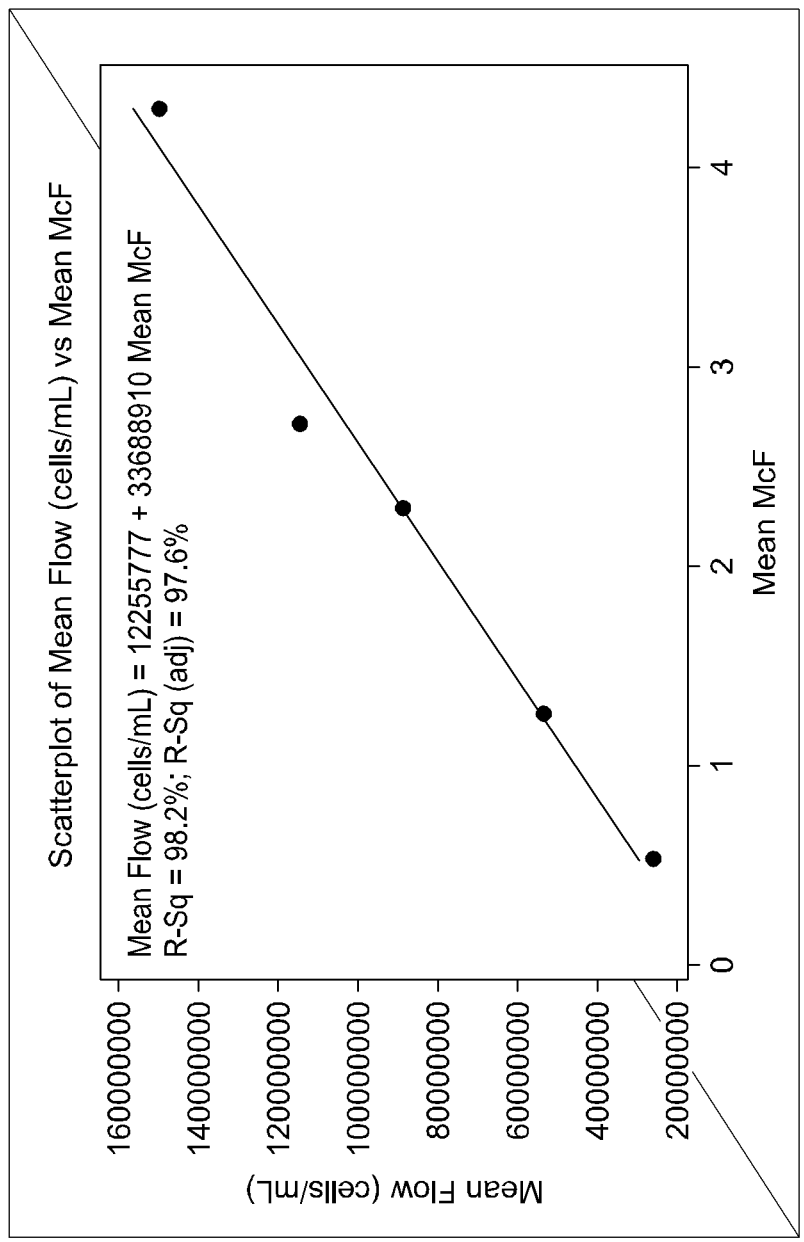
FIG. 8 is a chart depicting the correlation of nephelometry values and FACS counts for the enumeration of fixed *B. subtilis* cells.

After the cells are resuspended as depicted in block 738, the process 700 moves to block 740 and quantifies the bulk stocks. In some embodiments, the process 700 quantifies the bulk stocks by counting the cells. A variety of different techniques can be used to quantify the cells, including, for example, nephelometry, Fluorescence Activated Cell Sorting (FACS), and light microscopy such as, for example, a Helber counting chamber. In some embodiments, an accurate determination of the number of cells is important as the function of the SPC depends, to some extent, on the number of cells in the SPC. FIG. 8 depicts the correlation of nephelometry values and FACS counts for the enumeration of fixed B. subtilis cells. As depicted in FIG. 8, there is a good correlation between the nephelometry values and the FACS counts, which indicates that both methods can be used to enumerate the cells.

Returning again to FIG. 7, after the process 700 has determined the quantity of bulk stocks in block 740, the process moves to block 742 and verifies cellular integrity. In some embodiments, this verification can include, for example, verifying that the cells have not lysed, that they have been properly fixed, that they are the right type of cells, or any other desired verification.

After the process 700 has verified the cellular integrity, the process 700 moves to block 744 and stores the fixed cells. In some embodiments, a variety of techniques can be used to store the fixed cells. In some embodiments, the fixed cells can be stored in a temperature controlled environment. Advantageously, in some embodiments, control of the temperature in which the cells are stored can decrease cellular deterioration while in storage. In some embodiments, the cells can be stored at a temperature of −50° C., −10° C., 0° C., 4° C., 10° C., 20° C., 40° C., or any other desired temperature.

EXAMPLE 4

Stability of Fixed B. subtilis Cells

Ideally, specimen process controls should be stable over time. The following experiments, were performed in order to assess the stability of fixed B. subtilis cells. Advantageously, the fixation of the cells can allow storage of the cells for an extended period by decreasing the deterioration of the cells.

The cells used in these experiments were prepared using the process 700 described above. Specifically, cells were stored in HEPES buffer pH 5.5 at a temperature between 2-8° C. for up to 25 days. At four days, eleven days, and twenty five days, cell samples were removed from the buffer, divided into two groups and tested. In each of these experiments, one of the groups was exposed to ACP and the other group was not exposed to ACP. Briefly, the fixed B. subtilis cells were treated for twenty minutes at 50° C. in the presence or absence of ACP. After this treatment, the DNA was extracted from the B. subtilis cells using polyethyleneimine-coated magnetic affinity beads as described in U.S. Patent Publication No. 2010/0009351, the entirety of which is herein incorporated by reference. Following DNA extraction, a PCR amplification was performed on the extracted DNA, and real-time monitoring of fluorescence was used to detect target nucleic acids. The results are shown in FIG. 9.

Figure 9:
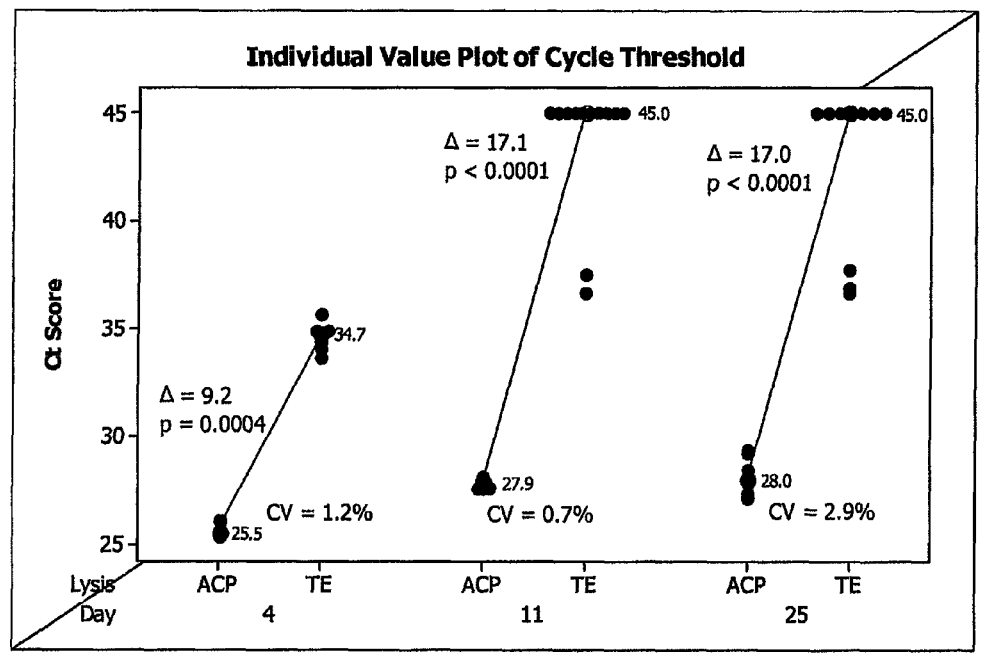
FIG. 9 is a chart depicting the results of a stability study performed on fixed *B. subtilis* cells.

As shown in FIG. 9, fixed B. subtilis cells maintained their cellular integrity until the cells were exposed to the lysis enzyme. Samples in which no amplification was detected were assigned a Ct value (cycle threshold value) of 45. There was a statistically significant difference between the Ct scores for the ACP and the non-ACP (TE) cells during each of these tests. This difference indicates that the B. subtilis cells maintained their integrity until they were exposed to the lysis enzyme, namely, ACP. Additionally, the coefficient of variation of the Ct values in the presence of ACP was <3%, which indicates a high degree of reproducibility between replicated testing events. These data demonstrate the long-term stability of fixed, vegetative-stage Bacillus cells, and thus confirm their usefulness as an SPC for molecular assays utilizing enzymatic lysis agents.

After the process 700 has stored the fixed cells, the process 700 moves from the second phase 704 relating to the fixation and quantification of cells to the third phase 706 relating to the manufacturing of a completed SPC. In some embodiments, the third phase 706 of the process begins when the process 700 moves to block 746 and formulates the SPC for drying. In some embodiments, the formulation of the SPC can include, for example, the addition of the desired number of cells and the addition of any other desired substance or composition.

After the process 700 formulates the SPC for drying as depicted in block 746, the process 700 moves to block 748 and dries the SPC. The drying of the SPC can be performed using a variety of techniques and a variety of environmental conditions. After the process 700 dries the SPC as depicted in block 748, the process moves to block 750 and package and stores the SPC. The packaging and storing of the SPC can comprise a variety of technique and use a variety of equipment.

In connection with the manufacturing phase 706 of the process 700, a variety of manufacturing processes were used. Table 4 below depicts some embodiments of manufacturing process that were used in connection with the manufacturing phase 706 of the process 700, and some of the results relating to the use of a specific manufacturing process in connection with the manufacture of the SPC.

TABLE 4

Processes for manufacture of SPC containing B. subtilis

| Manufacturing Process | Results |
| --- | --- |
| Lenticulation | Demonstrates poor solubility of excipient matrix |
| Tableting | Demonstrates poor solubility of excipients; adhesion of tablets to tooling |
| Convection drying | Fails to maintain cellular integrity |
| Cake Lyophilization | Demonstrates stability for 6 months at ambient temperature |
| Passive Evaporation | Demonstrates ability to meet preliminary specifications for maintenance of cellular integrity and reagent stability |
| Pellet Lyophilization 1, LyoSpheres | Demonstrates stability for 6 months at 2-25° C. |
| Pellet Lyophilization 2 | Demonstrates excipient(s) inhibitory to DNA extraction and/or PCR amplification/detection |

As seen in Table 4, the manufacturing processes relating to Cake Lyophilization and Pellet Lyophilization 1 demonstrate SPC stability for 6 months. As also seen in Table 4, some of the other manufacturing processes do not yield such positive results. A person of skill in the art will recognize that the results depicted in Table 4 are not comprehensive, and that such manufacturing techniques, as well as others could be used to create an SPC. A person of skill in the art will further recognize that while Table 4 includes some results which may indicate the benefit of certain manufacturing processes, these results should not be construed as requiring the use of, or excluding the potential use of any of the above-listed or otherwise known manufacturing processes.

Figure 10:
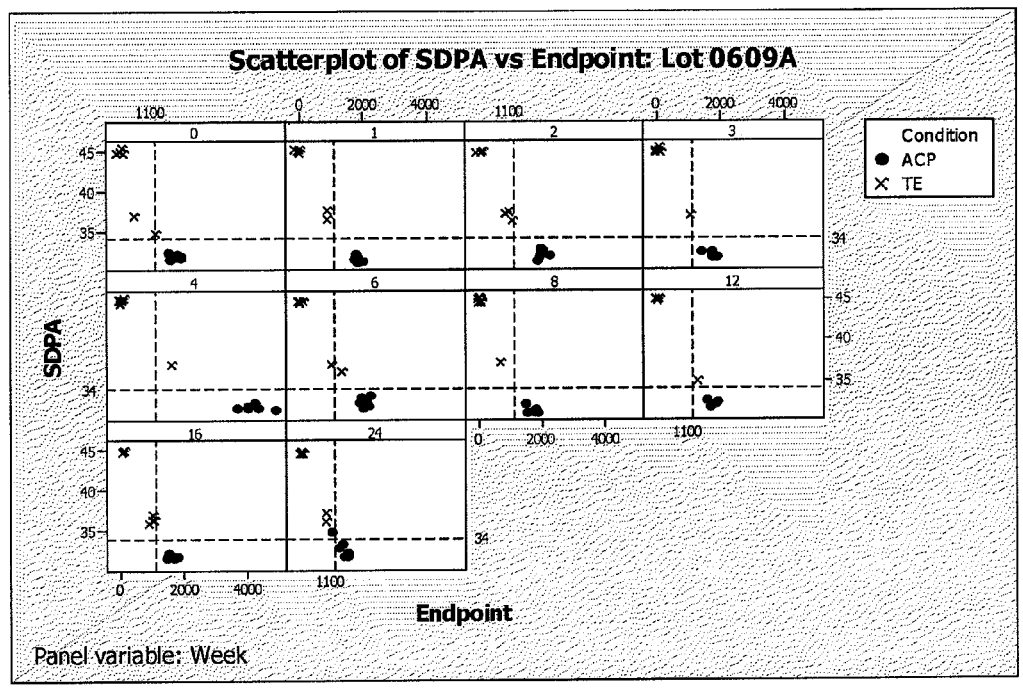
FIG. 10 is a chart depicting testing results relating to the stability over time of an SPC containing *B. subtilis* that is manufactured using cake lyophilization.
Figure 11A:
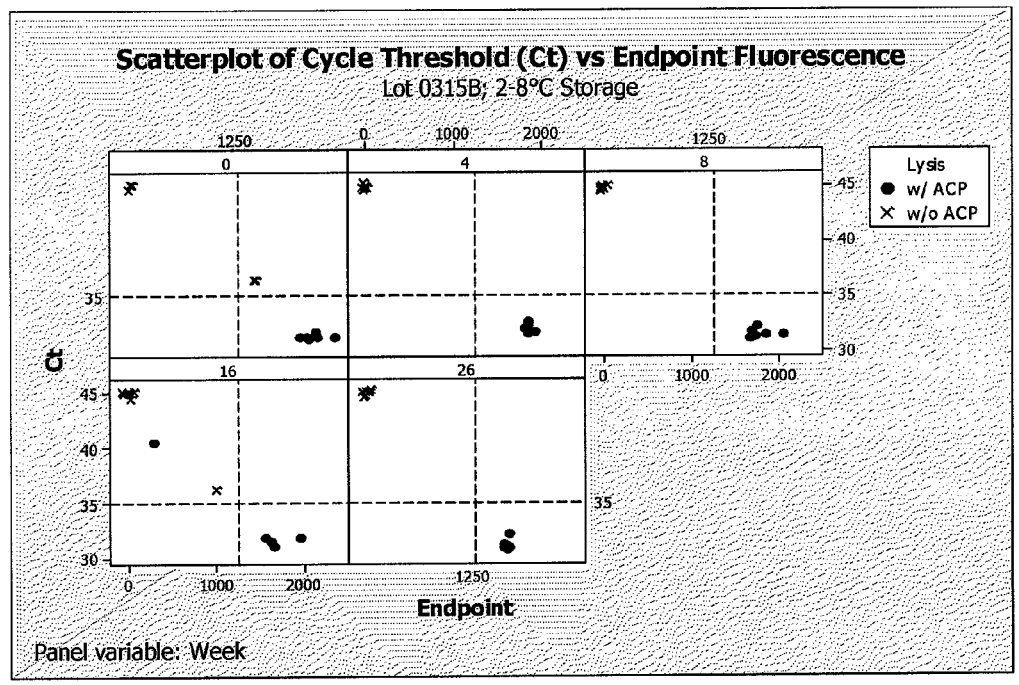
FIG. 11A is a chart depicting testing results relating to the stability over time of an SPC containing *B. subtilis* that was manufactured using pellet lyophilization and stored at a temperature of 2-8° C.
Figure 11B:
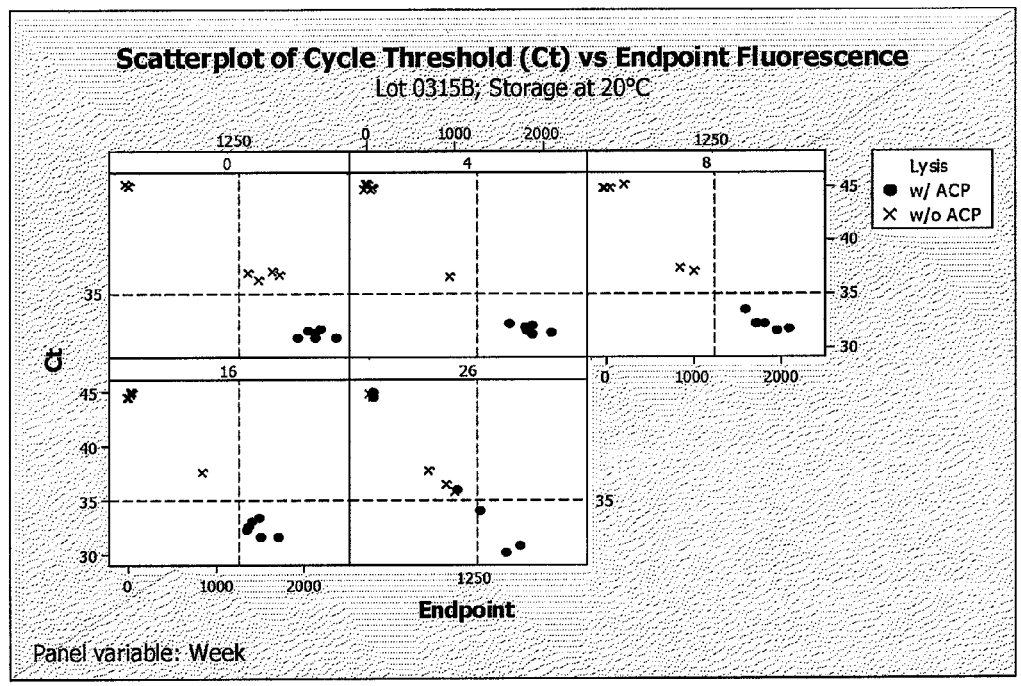
FIG. 11B is a chart depicting testing results relating to the stability over time of an SPC containing *B. subtilis* that was manufactured using pellet lyophilization and stored at a temperature of 20° C.

Two of the manufacturing processes described in Table 4 were tested, specifically, an SPC containing *B. subtilis* and manufactured using Cake Lyophilization and an SPC containing *B. subtilis* and manufactured using Pellet Lyophilization 1 was tested. The results of this testing is depicted in FIG. 10 and FIGS. 11A and 11B.

EXAMPLE 5

Effectiveness of Cake Lyophilization in Creating a Stable SPC Containing Fixed *B. subtilis* Cells The following experiments were performed in order to determine the effectiveness of cake lyophilization in creating a storable SPC containing fixed *B. subtilis* cells. In the experiments, such an SPC containing *B. subtilis* was stored and samples of the SPC containing *B. subtilis* were taken from storage and tested over a period of 24 weeks. Specifically, the SPC containing *B. subtilis* used in these experiments was prepared by overnight lyophilization of a suspension of formalin-fixed *B. subtilis* cells in a matrix comprising 2.3% w/v trehalose and 7.5% w/v dextran. Polypropylene tubes containing the lyophilized cake of SPC were sealed with foil and stored at ambient temperature in biaxially-oriented polyethylene terephthalate (BoPET) bags (Mylar®) containing desiccant.

Experiments were performed on the stored SPC after 0, 1, 2, 3, 4, 6, 8, 12, 16, and 24 weeks. In each of these experiments, the samples of the SPC containing *B. subtilis* were divided into two groups. One of these groups was ultimately exposed to 80 U of ACP and the other group was not exposed to ACP. In these experiments, the lyophilized cakes of *B. subtilis* were resuspended in a Tris-EDTA buffer containing Triton X-100. As discussed above, one portion of the sample was processed for DNA extraction in the presence of ACP (indicated in the chart as "ACP") and the other was processed in the absence of ACP (indicated in the chart as "TE"). The cells of both the group exposed to ACP and the control group that was not exposed to ACP were incubated for 20 min at 50° C. to facilitate cell lysis.

The results of the experiments are presented in FIG. 10 in terms of SDPA and endpoint fluorescence values. Throughout the study, lower SDPA and higher endpoint fluorescence values were obtained from the test condition (groups exposed to ACP) than the control condition (groups not exposed to ACP), indicating that the *B. subtilis* cells retained their integrity over time and that ACP enzyme activity was necessary to induce cell lysis and enable efficient DNA extraction, amplification and detection. At each time point the FIG. 10 shows a clear separation between the values obtained in the presence of ACP versus in the absence of ACP. This separation is indicated by the threshold lines drawn at endpoint=1100 and SDPA=34, and the separation results in a Mann-Whitney p-value of <0.01 for all cases. These results demonstrate the utility of lyophilized, fixed cells of recombinant *B. subtilis* as an SPC to verify the efficacy of ACP enzyme activity as well as DNA extraction, amplification and detection

EXAMPLE 6

Stability of LyoSpheres of SPC Containing Fixed *B. subtilis* Cells Stored at a Temperature Between 2-8° C. and at a Temperature of 20° C.

The following experiment was performed in order to determine the sability of SPC LyoSpheres containing fixed *B. subtilis* cells at a temperature between 2-8° C. and at a temperature of 20° C. The SPC LyoSpheres used in this experiment were manufactured using Pellet Lyophilization 1 as discussed in Table 4 above. In the experiments, one group of the SPC containing *B. subtilis* was stored at a temperature between 2-8° C. and another group of the SPC containing *B. subtilis* was stored at a temperature of 20° C. Samples of the SPC containing *B. subtilis* were taken from storage at intervals over a period of 26 weeks and tested. Specifically, the SPC was prepared in the form of LyoSpheres (Biolyph, LLC) and stored in polypropylene tubes that were sealed with foil and placed in biaxially-oriented polyethylene terephthalate (BoPET) (Mylar®) bags with a dessicant. One group of the bagged polypropylene tubes was stored at 2-8° C. in and the other group was stored at 20° C.

Experiments on the stored SPC were performed after 0, 4, 8, 16, and 26 weeks. In each of these experiments, the samples of the SPC containing *B. subtilis* stored at a temperature between 2-8° C. and stored at a temperature of 20° C. were divided into two groups. One of these groups was ultimately exposed to ACP and the other group was not exposed to ACP. In these experiments, LyoSpheres were removed from storage, resuspended in Tris-EDTA buffer containing Triton X-100 and processed for DNA extraction in the presence of 80 U of ACP (indicated in the chart as "w/ ACP") or in the absence of ACP (indicated in the chart as "w/o ACP"). In both the test group (the group exposed to ACP) and the control group (the group not exposed to ACP) conditions, cells were incubated for 20 min at 50° C. to facilitate cell lysis.

The results of these experiments are presented in FIGS. 11A and 11B in terms of cycle threshold ($C_t$) and endpoint fluorescence values. FIG. 11A presents the results of the experiments performed on the SPC containing *B. subtilis* and stored at a temperature between 2-8° C. As seen in FIG. 11A, throughout the study, lower cycle threshold values and higher endpoint fluorescence was obtained from the test condition (w/ACP) than the control condition (w/o ACP), indicating that the *B. subtilis* cells retained their integrity over time and that ACP enzyme activity was necessary to induce cell lysis and enable efficient DNA extraction, amplification and detection. At each time point FIG. 11A shows a clear separation between the values obtained in the presence of ACP versus in the absence of ACP. This separation is indicated by the threshold lines drawn at endpoint=1250 and Ct=35, and the separation results in a Mann-Whitney p-value of <0.05 for all cases.

FIG. 11B presents the results of the experiments performed on the SPC containing *B. subtilis* and stored at a temperature of 20° C. As seen in FIG. 11B, throughout the study, lower cycle threshold values and higher endpoint fluorescence was obtained from the test condition (w/ ACP) than the control condition (w/o ACP), indicating that the *B. subtilis* cells retained their integrity over time and that ACP enzyme activity was necessary to induce cell lysis and enable efficient DNA extraction, amplification and detection. At each time point FIG. 11B shows a clear separation between the values obtained in the presence of ACP versus in the absence of ACP. This separation is indicated by the threshold lines drawn at endpoint=1125 and Ct=35, and the separation results in a Mann-Whitney p-value of <0.01 for all cases except week 26.

The combined results of the experiments depicted in FIGS. 11A and 11B provide evidence of the utility of LyoSpheres of fixed cells of *B. subtilis* as an SPC to verify the efficacy of ACP enzyme activity as well as DNA extraction, amplification and detection.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein.

What is claimed is:

1. A method of determining the efficacy of enzymatic cell lysis, the method comprising: providing an internal control essentially free of contaminating extracellular DNA comprising a plurality of bacterial cells that have been fixed with a fixing compound and have been dried; mixing the internal control with a sample, lysing the internal control and the sample with a lysing agent, wherein said lysing agent comprises an enzymatic lysing agent; and detecting a lysis product of the internal control, wherein said plurality of bacterial cells essentially free of contaminating extracellular DNA are prepared from a population of bacterial cells wherein the growth of said population of bacterial cells is synchronized to generate a morphologically homogeneous population at the time of harvest, wherein said time of harvest is during vegetative cell growth, and wherein said plurality of bacterial cells are Gram-positive cells.

2. The method of claim 1, wherein the enzymatic lysing agent is a lysing enzyme selected from the group consisting of achromopeptidase (ACP), lysozyme, lysotraphin, zymolase, cellulase, mutanolysin, glycanase, proteinase K, pronase, and any combination thereof.

3. The method of claim 2, wherein the lysing enzyme is ACP.

4. The method of claim 1, wherein the bacterial cells are vegetative *Bacillus subtilis* cells.

5. The method of claim 4, wherein the lysing enzyme is ACP.

6. The method of claim 1, wherein the fixing compound is selected from the group consisting of formaldehyde, paraformaldehyde, glutaraldehyde, and any combination thereof.

7. The method of claim 1, wherein the fixed bacterial cells comprise recombinant cells.

8. The method of claim 6, wherein the recombinant cells comprise a heterologous control nucleic acid sequence.

9. The method of claim 1, wherein the plurality of fixed cells are washed to remove essentially all contaminating extracellular DNA prior to mixing the internal control with the sample.

10. The method of claim 1, wherein the plurality of fixed cells have been washed to remove essentially all contaminating extracellular DNA prior to being fixed.

11. The method of claim 1, wherein the internal control is dried by lyophilization.

12. The method of claim 1, wherein the detecting step comprises performing an amplification reaction and detecting an amplicon.

13. The method of claim 1, wherein the fixed cells are recombinant, *Bacillus* cells.

14. The method of claim 1, wherein said population of bacterial cells are fixed after harvesting, subsequently washed to remove essentially all contaminating extracellular DNA, and then lyophilized.

15. The method of claim 14, wherein the population of bacterial cells are vegetative *Bacillus subtilis* cells.

16. The method of claim 1, wherein said lysing agent further comprises an ionic detergent, a chaotrope, a reducing agent, or a combination thereof.

* * * * *